(12) United States Patent
 Piskun

(10) Patent No.: US 10,485,567 B2
(45) Date of Patent: *Nov. 26, 2019

(54) ENDOLUMINAL TREATMENT METHOD AND ASSOCIATED SURGICAL ASSEMBLY

(71) Applicant: Boston Scientific Scimed, Inc., Maple Grove, MN (US)

(72) Inventor: Gregory Piskun, Morganville, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/361,457

(22) Filed: Nov. 27, 2016

(65) Prior Publication Data

US 2017/0071620 A1    Mar. 16, 2017

Related U.S. Application Data

(60) Continuation of application No. 14/511,694, filed on Oct. 10, 2014, now Pat. No. 9,661,984, which is a
(Continued)

(51) Int. Cl.
*A61B 1/00*     (2006.01)
*A61B 17/32*    (2006.01)
(Continued)

(52) U.S. Cl.
CPC .. *A61B 17/320016* (2013.01); *A61B 1/00078* (2013.01); *A61B 1/00082* (2013.01);
(Continued)

(58) Field of Classification Search
CPC . A61B 1/00078; A61B 1/00082; A61B 1/018; A61B 1/0676; A61B 1/31;
(Continued)

(56) References Cited

U.S. PATENT DOCUMENTS

| 457,787 A | 8/1891 | Leisenring |
| 1,621,159 A | 3/1927 | Evans |

(Continued)

FOREIGN PATENT DOCUMENTS

| CN | 201200436 | 3/2009 |
| CN | 102018493 | 4/2011 |

(Continued)

OTHER PUBLICATIONS

European Search Report dated May 3, 2011 for European Patent Application No. 06789411.3.
(Continued)

*Primary Examiner* — Timothy J Neal

(57) ABSTRACT

A surgical instrument includes a hollow member having a sidewall provided with a window and a closure member movably connected to the hollow member for alternately covering and uncovering the window. The hollow member has a first clamping surface along an edge of the window, while the closure member has a second clamping surface opposing the first clamping surface and disposable substantially adjacent thereto in a clamping or closure configuration of the instrument. The instrument additionally comprises a tissue occlusion component mounted to at least one of the hollow member and the closure member for acting on tissues gripped between the first clamping surface and the second clamping surface, to couple the tissues to each other.

19 Claims, 12 Drawing Sheets

Related U.S. Application Data division of application No. 12/547,296, filed on Aug. 25, 2009, now Pat. No. 9,039,601, which is a division of application No. 11/197,965, filed on Aug. 5, 2005, now Pat. No. 8,100,822, which is a continuation-in-part of application No. 10/801,283, filed on Mar. 16, 2004, now Pat. No. 7,118,528.

(51) Int. Cl.

| | | |
|---|---|---|
| A61B 1/31 | (2006.01) | |
| A61B 17/072 | (2006.01) | |
| A61B 18/14 | (2006.01) | |
| A61B 18/22 | (2006.01) | |
| A61B 1/018 | (2006.01) | |
| A61B 1/045 | (2006.01) | |
| A61B 1/05 | (2006.01) | |
| A61B 1/06 | (2006.01) | |
| A61B 17/3205 | (2006.01) | |
| A61B 17/22 | (2006.01) | |
| A61B 17/34 | (2006.01) | |
| A61B 18/00 | (2006.01) | |
| A61B 17/00 | (2006.01) | |

(52) U.S. Cl.
CPC .............. *A61B 1/018* (2013.01); *A61B 1/045* (2013.01); *A61B 1/051* (2013.01); *A61B 1/0676* (2013.01); *A61B 1/31* (2013.01); *A61B 17/072* (2013.01); *A61B 17/22* (2013.01); *A61B 17/3205* (2013.01); *A61B 18/1442* (2013.01); *A61B 18/1445* (2013.01); *A61B 18/22* (2013.01); *A61B 2017/0034* (2013.01); *A61B 2017/00269* (2013.01); *A61B 2017/00893* (2013.01); *A61B 2017/07214* (2013.01); *A61B 2017/07221* (2013.01); *A61B 2017/32004* (2013.01); *A61B 2017/3452* (2013.01); *A61B 2018/005* (2013.01); *A61B 2018/0063* (2013.01); *A61B 2018/00428* (2013.01); *A61B 2018/00589* (2013.01)

(58) Field of Classification Search
CPC .......... A61B 17/320016; A61B 17/072; A61B 17/3205; A61B 18/1445; A61B 18/22; A61B 2017/07221; A61B 2017/32004; A61B 2018/00428
See application file for complete search history.

(56) References Cited

U.S. PATENT DOCUMENTS

| | | |
|---|---|---|
| 3,517,128 A | 6/1970 | Hines |
| 4,040,413 A | 8/1977 | Ohshiro |
| 4,083,369 A | 4/1978 | Sinnreich |
| 4,224,929 A | 9/1980 | Furihata |
| 4,295,464 A | 10/1981 | Shihata |
| 4,519,403 A | 5/1985 | Dickhudt |
| 4,611,594 A | 9/1986 | Grayhack et al. |
| 4,966,596 A | 10/1990 | Kuntz et al. |
| 5,025,778 A | 6/1991 | Silverstein |
| 5,059,199 A | 10/1991 | Okada |
| 5,087,265 A | 2/1992 | Summers |
| 5,112,310 A | 5/1992 | Grobe |
| 5,197,971 A | 3/1993 | Bonutti |
| 5,386,817 A | 2/1995 | Jones |
| 5,411,508 A | 5/1995 | Bessler et al. |
| 5,423,830 A | 6/1995 | Schneebaum et al. |
| 5,655,698 A | 8/1997 | Yoon |
| 5,716,321 A | 2/1998 | Kerin et al. |
| 5,722,103 A | 3/1998 | Walega |
| 5,776,097 A | 7/1998 | Massoud |
| 5,947,983 A | 9/1999 | Solar et al. |
| 5,954,731 A | 9/1999 | Yoon |
| 5,997,547 A | 12/1999 | Nakao et al. |
| 6,009,877 A | 1/2000 | Edwards |
| 6,042,596 A | 3/2000 | Bonutti |
| 6,119,913 A | 9/2000 | Adams et al. |
| 6,142,931 A | 11/2000 | Kaji |
| 6,142,933 A | 11/2000 | Longo et al. |
| 6,203,552 B1 | 3/2001 | Bagley et al. |
| 6,214,024 B1 | 4/2001 | Houser |
| 6,264,086 B1 | 7/2001 | McGuckin et al. |
| 6,302,311 B1 | 10/2001 | Adams et al. |
| 6,343,731 B1 | 2/2002 | Adams et al. |
| 6,405,732 B1 | 6/2002 | Edwards |
| 6,423,058 B1 | 7/2002 | Edwards et al. |
| 6,428,473 B1 | 8/2002 | Leonard et al. |
| 6,494,881 B1 | 12/2002 | Bales et al. |
| 6,616,603 B1 | 9/2003 | Fontana |
| 6,695,198 B2 | 2/2004 | Adams et al. |
| 6,805,273 B2 | 10/2004 | Bilotti et al. |
| 6,808,491 B2 | 10/2004 | Kortenbach et al. |
| 6,840,423 B2 | 1/2005 | Adams et al. |
| 6,866,178 B2 | 3/2005 | Adams et al. |
| 6,874,669 B2 | 4/2005 | Adams et al. |
| 6,913,610 B2 | 7/2005 | Nakao |
| 6,923,806 B2 | 8/2005 | Hooven et al. |
| 6,938,814 B2 | 9/2005 | Sharma et al. |
| 7,014,646 B2 | 3/2006 | Adams et al. |
| 7,059,331 B2 | 6/2006 | Adams et al. |
| 7,169,115 B2 | 6/2007 | Nobis et al. |
| 7,276,066 B2 | 10/2007 | Ouchi |
| 7,396,329 B2 | 7/2008 | Nakao |
| 7,445,598 B2 | 11/2008 | Orban |
| 7,918,787 B2 | 4/2011 | Saadat |
| 7,959,559 B2 | 6/2011 | Yamaya |
| 8,007,508 B2 | 8/2011 | Cox |
| 8,277,373 B2 | 10/2012 | Maahs et al. |
| 8,506,479 B2 | 8/2013 | Piskun et al. |
| 8,517,933 B2 | 8/2013 | Mohr |
| 8,608,652 B2 | 12/2013 | Voegele et al. |
| 8,764,630 B2 | 7/2014 | Yamatani |
| 8,777,961 B2 | 7/2014 | Cabrera et al. |
| 8,932,326 B2 | 1/2015 | Riina et al. |
| 8,979,884 B2 | 3/2015 | Milsom et al. |
| 9,050,004 B2 | 6/2015 | Diao et al. |
| 9,161,746 B2 | 10/2015 | Piskun et al. |
| 9,168,053 B2 | 10/2015 | Cox |
| 9,259,233 B2 | 2/2016 | Gruber et al. |
| 9,370,379 B2 | 6/2016 | Osman |
| 9,375,224 B2 | 6/2016 | Jansen |
| 9,661,984 B2 * | 5/2017 | Piskun .................. A61B 1/31 |
| 2001/0004947 A1 | 6/2001 | Lemke et al. |
| 2001/0047169 A1 | 11/2001 | McGuckin, Jr. et al. |
| 2001/0049497 A1 | 12/2001 | Kalloo et al. |
| 2002/0123748 A1 | 9/2002 | Edwards et al. |
| 2002/0183593 A1 | 12/2002 | Chin et al. |
| 2002/0193660 A1 | 12/2002 | Weber et al. |
| 2003/0023143 A1 | 1/2003 | Abe et al. |
| 2003/0050663 A1 | 3/2003 | Khachin et al. |
| 2003/0074015 A1 | 4/2003 | Nakao |
| 2003/0135230 A1 | 7/2003 | Massey et al. |
| 2003/0225432 A1 | 12/2003 | Baptiste et al. |
| 2003/0225433 A1 | 12/2003 | Nakao |
| 2004/0034278 A1 | 2/2004 | Adams |
| 2004/0082859 A1 | 4/2004 | Schaer |
| 2004/0158263 A1 | 8/2004 | McAlister et al. |
| 2004/0204725 A1 | 10/2004 | Bayer |
| 2004/0249367 A1 | 12/2004 | Saadat et al. |
| 2005/0177105 A1 | 8/2005 | Shalev |
| 2005/0234297 A1 | 10/2005 | Devierre |
| 2005/0234299 A1 | 10/2005 | Eitenmuller et al. |
| 2005/0240147 A1 | 10/2005 | Makower et al. |
| 2005/0251111 A1 | 11/2005 | Saito et al. |
| 2005/0251177 A1 | 11/2005 | Saadat et al. |
| 2005/0272977 A1 | 12/2005 | Saadat et al. |
| 2006/0074277 A1 | 4/2006 | Yoshida |
| 2006/0100480 A1 | 5/2006 | Ewers et al. |
| 2006/0189845 A1 | 8/2006 | Maahs et al. |
| 2006/0191975 A1 | 8/2006 | Adams et al. |
| 2006/0247662 A1 | 11/2006 | Schwartz |

(56) References Cited

U.S. PATENT DOCUMENTS

| | | |
|---|---|---|
| 2006/0264706 A1 | 11/2006 | Piskun |
| 2007/0005093 A1 | 1/2007 | Cox |
| 2007/0021778 A1 | 1/2007 | Carly |
| 2007/0255207 A1 | 11/2007 | Hangai et al. |
| 2007/0287886 A1 | 12/2007 | Saadat |
| 2007/0287889 A1 | 12/2007 | Mohr |
| 2007/0293724 A1 | 12/2007 | Saadat et al. |
| 2008/0045842 A1 | 2/2008 | Furnish |
| 2008/0051629 A1 | 2/2008 | Sugiyama et al. |
| 2008/0132835 A1 | 6/2008 | Nagamatsu et al. |
| 2008/0161645 A1 | 7/2008 | Goldwasser et al. |
| 2008/0188868 A1 | 8/2008 | Weitzner et al. |
| 2008/0228209 A1 | 9/2008 | DeMello et al. |
| 2008/0249534 A1 | 10/2008 | Gruber et al. |
| 2008/0269557 A1 | 10/2008 | Marescaux et al. |
| 2008/0269559 A1 | 10/2008 | Miyamoto et al. |
| 2008/0275300 A1 | 11/2008 | Rothe et al. |
| 2008/0300454 A1 | 12/2008 | Goto |
| 2009/0018500 A1 | 1/2009 | Carter et al. |
| 2009/0030369 A1 | 1/2009 | Nagamatsu et al. |
| 2009/0149716 A1 | 6/2009 | Diao et al. |
| 2009/0156996 A1 | 6/2009 | Milsom et al. |
| 2009/0287046 A1 | 11/2009 | Yamatani |
| 2009/0312645 A1 | 12/2009 | Weitzner et al. |
| 2010/0010296 A1 | 1/2010 | Piskun et al. |
| 2010/0049137 A1 | 2/2010 | Fischer, Jr. |
| 2010/0106240 A1 | 4/2010 | Duggal et al. |
| 2010/0152590 A1 | 6/2010 | Moore et al. |
| 2011/0065985 A1 | 3/2011 | Wehrheim |
| 2011/0077498 A1 | 3/2011 | McDaniel |
| 2011/0160538 A1 | 6/2011 | Ravikumar et al. |
| 2011/0172491 A1 | 7/2011 | Piskun et al. |
| 2011/0224494 A1 | 9/2011 | Piskun et al. |
| 2011/0245858 A1 | 10/2011 | Milsom et al. |
| 2011/0306832 A1 | 12/2011 | Bassan et al. |
| 2012/0083797 A1 | 4/2012 | Cabrera et al. |
| 2012/0095498 A1 | 4/2012 | Stefanchik et al. |
| 2012/0109178 A1 | 5/2012 | Edwards et al. |
| 2012/0165604 A1 | 6/2012 | Stokes et al. |
| 2013/0090527 A1 | 4/2013 | Axon |
| 2013/0172828 A1 | 7/2013 | Kappel et al. |
| 2013/0274553 A1 | 10/2013 | Piskun et al. |
| 2013/0317303 A1 | 11/2013 | Deshmukh et al. |
| 2013/0324795 A1 | 12/2013 | Nakajima et al. |
| 2014/0316379 A1 | 10/2014 | Sonderegger et al. |
| 2015/0150436 A1 | 6/2015 | Cornhill et al. |
| 2015/0157192 A1 | 6/2015 | Piskun et al. |
| 2015/0265268 A1 | 9/2015 | Diao et al. |
| 2015/0265818 A1 | 9/2015 | Piskun et al. |
| 2015/0272564 A1 | 10/2015 | Piskun et al. |
| 2015/0351890 A1 | 12/2015 | Levin et al. |
| 2016/0038172 A1 | 2/2016 | Cox |
| 2016/0081702 A1 | 3/2016 | Kan et al. |
| 2016/0106466 A1 | 4/2016 | Gruber et al. |
| 2016/0157843 A1 | 6/2016 | Dickson et al. |
| 2016/0374658 A1 | 12/2016 | Piskun |

FOREIGN PATENT DOCUMENTS

| | | |
|---|---|---|
| CN | 102695541 A | 9/2012 |
| EP | 0163502 A2 | 12/1985 |
| EP | 1588670 A1 | 10/2005 |
| EP | 2512577 A2 | 10/2012 |
| GB | 2365340 | 2/2002 |
| JP | S63292935 A | 11/1988 |
| JP | H08317928 A | 12/1996 |
| JP | H08336538 A | 12/1996 |
| JP | 2533732 Y2 | 4/1997 |
| JP | H1028691 A | 2/1998 |
| JP | 2000166936 A | 6/2000 |
| JP | 2000-325303 | 11/2000 |
| JP | 2001527429 A | 12/2001 |
| JP | 2004154485 A | 6/2004 |
| JP | 2004529708 A | 9/2004 |
| JP | 2005/046274 | 2/2005 |
| JP | 2007511247 A | 5/2007 |
| JP | 2008528239 A | 7/2008 |
| JP | 2008536552 A | 9/2008 |
| JP | 2009523054 A | 6/2009 |
| JP | 2009279406 A | 12/2009 |
| JP | 2010511440 A | 4/2010 |
| JP | 2011072782 A | 4/2011 |
| JP | 2012075908 A | 4/2012 |
| JP | 2013514827 A | 5/2013 |
| WO | WO 91/01773 | 2/1991 |
| WO | WO 9635469 | 11/1996 |
| WO | 9640347 A1 | 12/1996 |
| WO | 03000139 A1 | 1/2003 |
| WO | 2004103430 A2 | 12/2004 |
| WO | 2006110275 A2 | 10/2006 |
| WO | 2007081601 A2 | 7/2007 |
| WO | WO 2008/011163 | 1/2008 |
| WO | WO 2009/059296 | 5/2009 |
| WO | WO 2009/076176 | 6/2009 |
| WO | WO 2009/117696 | 9/2009 |
| WO | WO 2011/084616 | 7/2011 |
| WO | 2012068048 A1 | 5/2012 |
| WO | 2012114569 A1 | 8/2012 |
| WO | 2013050880 A2 | 4/2013 |
| WO | 2013192116 A1 | 12/2013 |
| WO | 2014200737 A1 | 12/2014 |
| WO | 2015026968 A1 | 2/2015 |
| WO | 2015191125 A1 | 12/2015 |

OTHER PUBLICATIONS

Written Opinion dated Jun. 20, 2007 for International Application No. PCT/US06/30464.
Chinese Office Action dated May 12, 2009 for Chinese Application No. 200680028706.2.
European Search Report dated Jun. 1, 2014 for International Application No. PCT/US2014/040429.
International Search Report and Written Opinion dated May 6, 2016 for International Application No. PCT/US2016/016911.
International Search Report and Written Opinion for PCT application No. PCT/US17/50685, dated Dec. 14, 2017, 16 pages.
International Search Report and Written Opinion (dated May 9, 2018), for PCT/US17/68991 13 pages.
The Extended PCT Search Report Application No. PCT/US2016/031355, dated Jul. 18, 2016.
European Communication for European Patent Application No. 14733912.1, dated Jun. 11, 2018, 2 pages.
International Search Report and Written Opinion for International Application No. PCT/US18/14388, dated Jun. 19, 2018, 9 pages.
International Search Report and Written Opinion for PCT/US10/60802, dated Aug. 24, 2011, 12 pages.
International Search Report and Written Opinion for International Application No. PCT/US18/21779, dated Jun. 14, 2018, 10 pages.

* cited by examiner

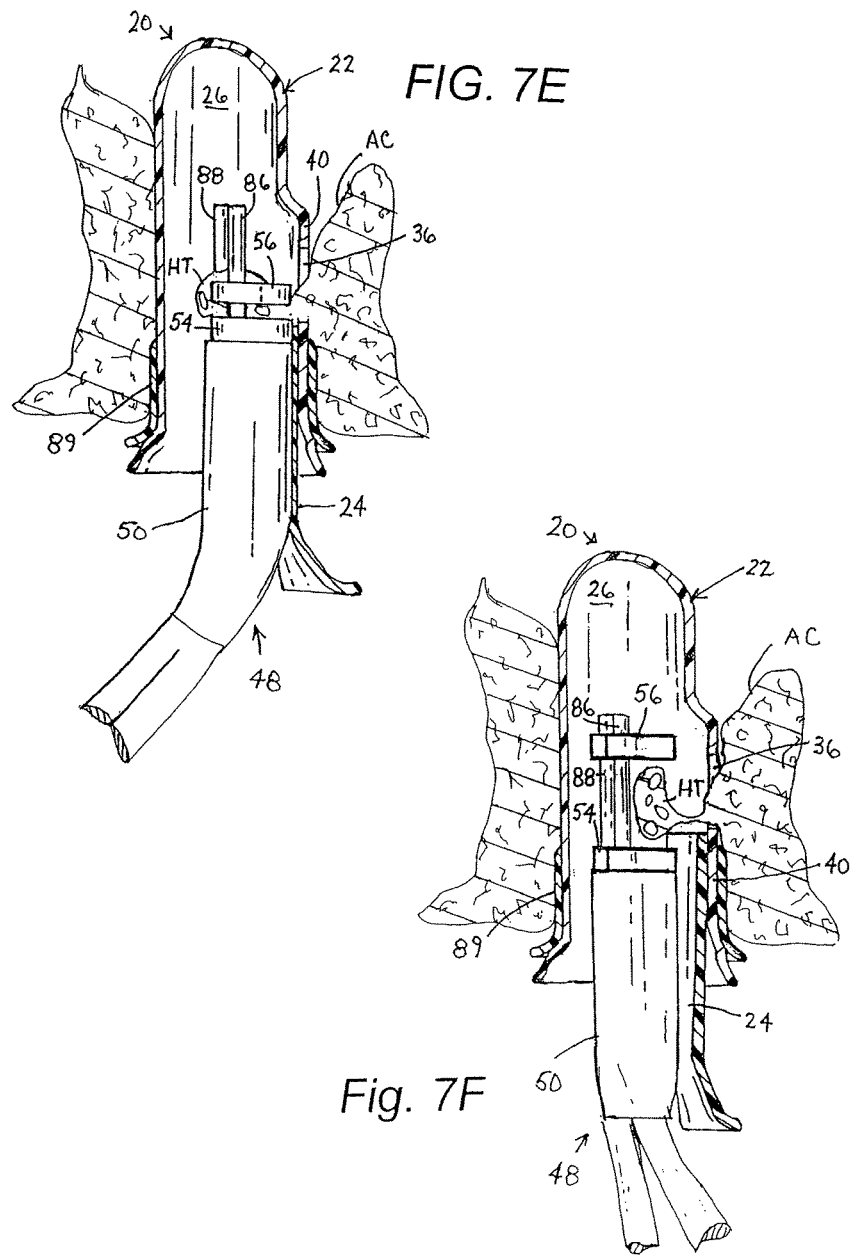

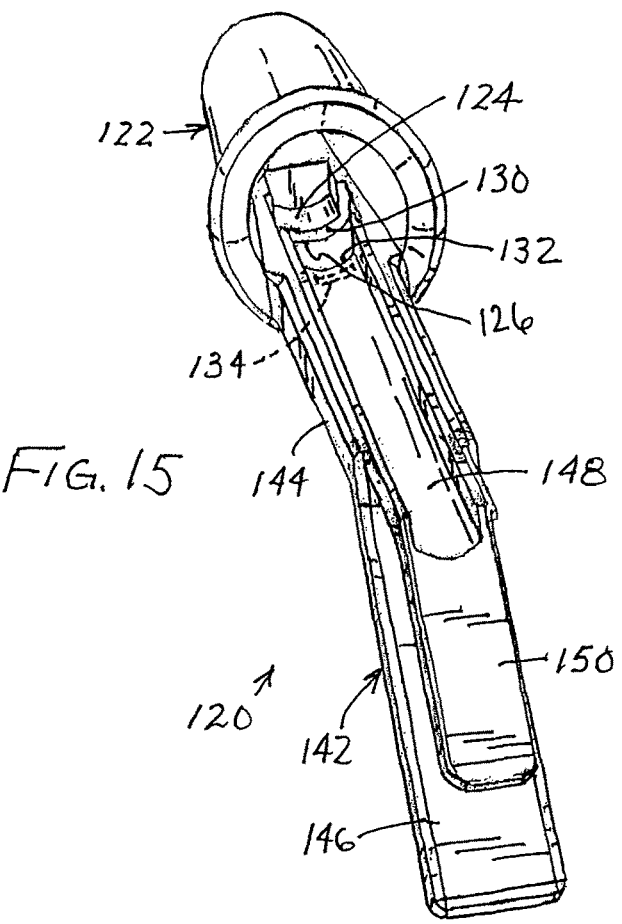
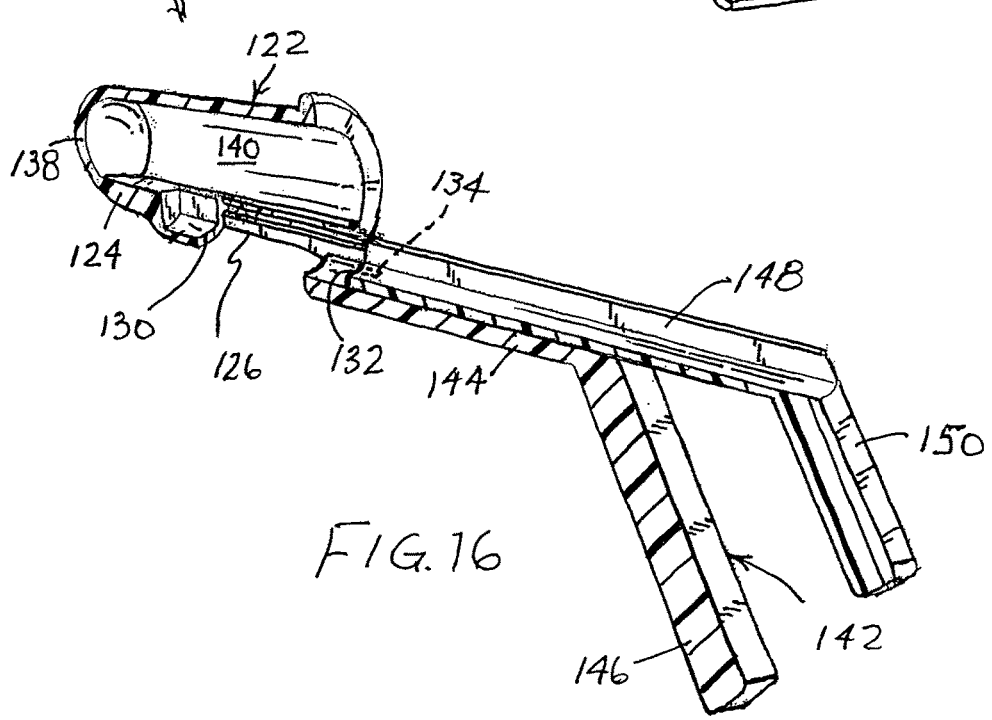

ENDOLUMINAL TREATMENT METHOD AND ASSOCIATED SURGICAL ASSEMBLY

CROSS-REFERENCE TO RELATED APPLICATION

This application is a continuation of application Ser. No. 14/511,694, filed Oct. 10, 2014 which is a divisional of application Ser. No. 12/547,296, filed Aug. 25, 2009, now U.S. Pat. No. 9,039,601, which is a divisional of application Ser. No. 11/197,965, filed on Aug. 5, 2005, now U.S. Pat. No. 8,100,822, which is a continuation-in-part of application Ser. No. 10/801,283, filed Mar. 16, 2004, now U.S. Pat. No. 7,118,528. The entire contents of each of these applications are incorporated herein by reference.

FIELD OF THE INVENTION

This invention relates to the surgical treatment of tissue masses located inside the human body and particularly along the walls of hollow internal organs such as the colon. The invention is particularly but not exclusively suitable for use in the treatment of hemorrhoids. This invention also relates, more specifically, to a hemorrhoid treatment method wherein the base of a hemorrhoid is compressed by jaws of a clamping instrument, and then the vascular supply of the hemorrhoid is occluded by application of an impact or energy. This invention also relates to an instrument assembly designed to accomplish this task.

BACKGROUND OF THE INVENTION

There are a variety of abnormal conditions in the human or animal body which are limited to the internal lining of the hollow organs. Colonic polyps, intestinal arteriovenous malformations, endothelial vascular lesions, abnormal venous valves, and complicated internal hemorrhoids are just few examples. Other conditions may involve the full thickness of the wall of the hollow organ as in a colonic perforation, an invading malignant tumor, etc. An endoluminal approach to such abnormal conditions may be highly beneficial to the patient since a surgical access trauma is essentially eliminated.

One common condition that is relatively easily treated using an endoluminal approach are complex hemorrhoids. These are traditionally treated utilizing a variety of interventional and non-interventional endoluminal methods. An immediate proximity of internal hemorrhoids to the external orifice allows for a fairly easy access. Several technologies are available on the market and are reviewed below. They, however, carry well-known limitations related to cost, technical complexity and/or poor clinical outcomes.

Hemorrhoidal disease is a very common condition, affecting more than half of people at age 50. Approximately 500,000 patients receive one or another type of interventional treatment annually in the United States for symptomatic hemorrhoids. Approximately 160,000 patients a year in the U.S. undergo surgical excision of hemorrhoids.

The term "hemorrhoid" is generally used to refer to the disturbing perianal symptoms related to vascular complexes in the lower rectum and anus. This is usually associated with enlargement of this naturally occurring vascular tissue, which is responsible for its subsequent bleeding, prolapsing, thrombosis, itching, burning, etcetera. The word "hemorrhoids" originates from Greek "haimorrhoos" (haimo—hemo+rhein—to flow), which means "flowing with blood." The word "pile" is a synonym for hemorrhoid, which originates from Latin "pila"—"ball."

Repetitive straining due to constipation appears to be a leading factor in forming and progressing of hemorrhoids. The chances of having symptomatic hemorrhoids increase with age, pregnancy, obesity, sedimentary life, heavy lifting and genetic predisposition.

The rectum is arbitrarily separated from the anus by the so-called dentate line. Rectal mucosa is free of pain receptors. The procedures limited to the rectal mucosa, therefore, generally are not associated with pain. In contrast, anal mucosa contains many pain receptors and is, therefore, very sensitive to painful stimuli. Hemorrhoids, located in the rectum, are called internal. Internal hemorrhoids are located within the submucosal layer. External hemorrhoids are located in the anus. Internal and external hemorrhoids have generally different clinical presentation and complications. Internal hemorrhoids are prone to bleeding and prolapsing outside of the anal ring. A prolapsed internal hemorrhoid can easily become traumatized and strangulated by a spastic anal sphincter. External hemorrhoids may rupture, causing painful subcutaneous lumps in the perianal area, which is frequently referred to as "thrombosed external hemorrhoids". Thrombosis of external hemorrhoid may lead to ulceration of the overlying tissues and bleeding. Both types of hemorrhoids may be responsible for perianal discomfort, itching, irritation, impeding of perianal hygiene, loss of work time and measurable decrease of quality of life.

Treatment is tailored to the type and severity of hemorrhoids. Pharmacological treatment, which is aimed at the regulation of defecation and symptomatic relief, is notorious for having only temporary and frequently incomplete effect. Current interventional, non-excisional, therapies are designed to obliterate blood supply to part of or to the entire hemorrhoid (rubber band ligation, infrared coagulation, injection sclerotherapy, ultrasound guided hemorrhoidal artery ligation). These have modest, inconsistent clinical success with frequent recurrences.

Rubber band ligation is the most popular method of treatment of hemorrhoids in the United States. The technique was described by Blaisdell in 1963. It is quick and not expensive. In this procedure, some hemorrhoidal tissue is pulled into the ligator and a rubber band is placed around the base of the pulled tissue. This causes essentially a strangulation of the blood supply to a portion of the internal hemorrhoid and its overlying rectal mucosa. An ischemic necrosis and autoamputation of the hemorrhoid follows in a few days, leaving an open rectal wound, which heals over several days. Significant postprocedural pain, affecting daily routine, is rare and is probably related to the placement of the band too close to the dentate line (pain-sensitive area). Although rubber band ligation is very effective for immediate bleeding control of small internal hemorrhoids, frequently several treatments of a single larger hemorrhoid are required in order to achieve substantial size reduction. Since the significant portion of the hemorrhoid is usually not removed, recurrences are frequent. In addition, since this treatment leaves the patient with an open wound in the anus for several days or weeks, rubber band ligation might be rendered unsuitable for HIV-positive patients and requires demanding preparation for patients with inherited, acquired and iatrogenic coagulopathy.

Sclerotherapy is another method to treat first- and second-degree internal hemorrhoids. The delivery of a sclerosing agent is accomplished through a single fine needle, attached to the syringe, and is intended to be within the vascular lumen. Since a hemorrhoid is essentially a ball of multiple twisted vascular lumens, it is virtually impossible to deliver sclerosing agent with the desired precision. The rates of complications and recurrence are high.

Ultrasound guided hemorrhoidal artery ligation involves manual suturing of the rectal tissues containing the hemorrhoial artery. The artery is located by the ultrasound. A resulting regression of the corresponding internal hemorrhoid is expected. Since suture-ligation is performed above the internal hemorrhoid in the pain-insensitive zone, the procedure should be painless. The technique is demanding and is highly dependent on the operator's experience and dexterity. Inexperience or lack of skill is responsible for both "missing" the hemorrhoidal artery and inadvertent rectal and vascular injuries. Hemorrhoidal artery injuries with resulting severe bleeding, rectal wall injury, etc. have been reported. Recurrences are frequent.

Infrared coagulation of a hemorrhoidal artery involves delivery of the infrared coagulation energy to the hemorrhoidal artery and causes subsequent regression of the corresponding internal hemorrhoid. Since the exact location of the artery is not known and is only presumed to be just proximal to the internal hemorrhoid, several blind infrared firings are required to improve the chance of reaching the hidden target. Several sessions of treatments in a time span of several weeks is recommended. The proper application of the infrared probe is more difficult with larger hemorrhoids due to obscurity of the interface between the probe and mucosa. Recurrences are frequent.

None of the above described techniques adequately addresses tissue redundancy and tissue prolapse, which frequently accompany more advanced stages (late $2^{nd}$, $3^{rd}$ and $4^{th}$) of hemorrhoidal disease and, therefore, can be considered only for the treatment of $1^{st}$ and early $2^{nd}$ stages of internal hemorrhoids. Even then, the rate of recurrence is substantial, reflecting the deficiencies of the existing methods.

The only approach which has been found to be consistently effective in the long-lasting control of the hemorrhoidal symptoms is the surgical excision of the hemorrhoids. There are two main methods of surgical excision of internal hemorrhoids: traditional surgical excision (longitudinal hemorrhoidectomy) and the so-called Procedure for Prolapse and Hemorrhoids or PPH (transverse hemorrhoidectomy with circular stapler).

Traditional surgical excision of hemorrhoids is a very effective but debilitating form of treatment. The hemorrhoidal tissue essentially is removed in longitudinal fashion down to the underlying internal sphincter. Traditional surgical excision almost invariably extends the anal trauma to and beyond the dentate line, thus causing severe postoperative pain. The technique is highly dependent on the technical skill of the operator. Surgical excision of hemorrhoids requires anesthesia and causes severe perianal pain for several weeks and significant loss of work time.

The so-called Procedure for Prolapse and Hemorrhoids (PPH) involves circumferential excision of the rectal mucosa and submucosal layer with a circular stapler, proximal to the internal hemorrhoids. The procedure is essentially directed towards a radical devascularization of the hemorrhoids while the hemorrhoidal tissue itself is left to ischemically regress. Since excision is done in the pain insensitive area (above the dentate line), a decreased postoperative pain and faster recovery when compared to traditional hemorrhoidectomy are observed. The internal hemorrhoids purportedly shrink within four to six weeks after the procedure. Advocates of PPH claim less pain and faster recovery, but the technique requires anesthesia and a demanding technical and instrumental set-up. In addition, this technique creates substantial circumferential rectal trauma, which is clearly excessive in the majority of cases when only 1 or 2 hemorrhoids are enlarged. Serious complications have been reported. A substantial circumferential injury of the anal canal and subsequent scarring may cause rectal stricture (narrowing), which is debilitating and difficult to treat. The technique requires massive anal dilation in order to accommodate a large head assembly of the circular stapler, which by itself presents an additional source of postoperative anal discomfort and potential anal trauma (anal fissures, bleeding, etc.). The main achievement of PPH technique over traditional hemorrhoidectomy is the placement of the surgical injury line in transverse fashion above the dentate line.

In summary, although many minimally invasive techniques have been introduced to treat symptomatic internal hemorrhoids, these entail a high rate of recurrence and a need for repetitive procedures. Approximately 15-20% of patients undergoing an intervention for treatment of their internal hemorrhoids require surgical excision of hemorrhoids, mainly because the current non-excisional techniques do not address or address inadequately (rubber band ligation) the accompanying anal mucosal prolapse and tissue redundancy. Some groups of patients, such as HIV-positive patients, and patients with spinal cord injuries, coagulopathy, etc, have absolute or relative contraindications to the existing techniques. The Procedure for Prolapse and Hemorrhoids addresses many of the deficiencies of the existing techniques, but involves a demanding technical and instrumental set-up, requires general or regional anesthesia, and is designed to perform frequently unnecessary circumferential rectal injury.

There is a need, therefore, for a device which allows fast and effective treatment of hemorrhoids in minimally invasive (innocent tissues are spared) and painless fashion (excisional line is placed above the dentate line).

OBJECTS OF THE INVENTION

It is an object of the present invention to provide an improved method for the surgical treatment of internal tissues located along the walls of internal body organs or lumens such as the colon.

It is a more specific object of the present invention to provide such a method that is useful in the treatment of hemorrhoidal tissues.

It is another specific object of the present invention to provide a surgical method that is less traumatic than prior art methods for the surgical treatment of hemorrhoids.

A further relatively specific object of the present invention is to provide a surgical method for the treatment of hemorrhoids, that may appropriately be carried out in an office, rather than requiring an operating room.

It is a related object of the present invention to provide an anoscope that may be used in carrying out the method of the invention.

Another related object of the present invention is to provide an instrument assembly including a tissue occlusion device that may be used in carrying out the method of the invention. A further object of the present invention is to provide a surgical instrument assembly for treating one or more hemorrhoids with any severity of enlargement and prolapse.

Yet another object of the present invention is to provide a method and/or an associated instrument assembly that may be used with an endoscope to access surgical sites in natural body lumens where the surgical sites are far removed from natural body openings.

These and other objects of the present invention will be apparent from the drawings and descriptions herein. Although every object of the invention is believed to be attained in at least one embodiment of the invention, there is not necessarily any single embodiment that attains all of the objects of the invention.

SUMMARY OF THE INVENTION

The present invention is directed in part to providing a device and an associate method for the treatment of hemorrhoids. The device can also be utilized for the treatment of other pathologies in locations remote that are from natural body openings. Accordingly, the invention is directed in part to an endoluminal intervention assembly that includes an accessory system for the delivery and support (optically and mechanically) of instrumentation to surgical sites remote from the natural openings.

A surgical instrument comprises, in accordance with the present invention, a hollow member having a sidewall provided with a window, and a closure member movably connected to the hollow member for alternately covering and uncovering the window. The hollow member has a first clamping surface along an edge of the window, while the closure member has a second clamping surface opposing the first clamping surface and disposable substantially adjacent thereto in a clamping or closure configuration of the instrument. The instrument additionally comprises a tissue occlusion component mounted to at least one of the hollow member and the closure member for acting on tissues gripped between the first clamping surface and the second clamping surface, to couple the tissues to each other.

In an endoscopic embodiment of the invention, the hollow member has a channel for receiving an insertion member of an endoscope, and the hollow member includes a chamber located laterally relative to the channel, the window communicating with the chamber. The closure member may be slidably inserted in another channel in the hollow member. The hollow member may be provided with a plurality of light access openings for permitting visual inspection of the chamber from outside the hollow member. The hollow member or the endoscope is in this case provided with light guide components such as optical fiber bundles for conveying illumination to the chamber and for transmitting images from the chamber to a viewer such as a video monitor or eyepiece. The hollow member of the endoscope may be further provided with one or more working channels that communicate at the distal ends with the chamber for enabling the insertion of endoscopic instrument tips into the chamber.

In accordance with another feature of the present invention, the sidewall of the hollow member is curved and at least one of the first clamping surface and the second clamping surface has a curved form, e.g., a C shape or U shape.

Where the closure member is slidably connected to the hollow member, the first clamping surface and the second clamping surface may stay substantially parallel to one another during opening and closing strokes of the closure member. Also, where the hollow member has a longitudinal axis, the first clamping surface and the second clamping surface may extend in planes oriented substantially perpendicularly to the axis, while the closure member is movable parallel to the axis.

In an alternate embodiment of the present invention, the hollow member is provided with a channel, the closure member is disposed in part in the channel, and the window communicates with the channel.

Pursuant to one embodiment of the present invention, the hollow member is closed at one end, and is provided with a handle at an opposite end. The closure member may also be provided, at an end opposite the second clamping surface, with a handgrip extending parallel to the handle.

The tissue occlusion component may be a stapling mechanism, an injection mechanism connectable to a reservoir of a sclerosing composition, or optical fibers connectable to a source of laser radiation. Other kinds of tissue occlusion device will be apparent to those skilled in the art.

A surgical instrument comprises, in accordance with the present invention, a hollow body defining a longitudinal channel, the hollow body being at least partially open at a proximal end, the hollow body having a sidewall provided with a window spaced from the proximal end. The surgical instrument further comprises a shutter or closure member movably mounted to the hollow body to cover the window during a positioning of the hollow body in a body lumen, the shutter or closure member being removable from the window to permit organic tissues to protrude through the window.

The window may be located in a bulging portion of a sidewall of the hollow body of the instrument.

In an embodiment of the invention particularly suitable for use with an endoscope, (a) the hollow body has a chamber disposed in the bulging portion, (b) the window communicates with the chamber, (c) the hollow member is formed with a partition separating the channel from the chamber, and (d) the channel is dimensioned for receiving an insertion member of an endoscope. Thus, in this embodiment of the invention, the instrument is designed for coupling to an endoscope for insertion into a patient together with a distal end portion of the endoscope. The the shutter or closure member may be slidably disposed in the hollow body.

A surgical method in accordance with the present invention utilizes an instrument assembly including a hollow body member having a sidewall formed with a window and further including a tissue occlusion component, the occlusion component defining a pair of jaws, at least one of the jaws including an arcuate clamping surface. The method comprises (i) inserting the hollow body member into a body lumen of a patient, (ii) manipulating the hollow body member so that organic tissues protrude through the window into the hollow body member, (iii) after the protruding of the tissues through the window, manipulating the occlusion component so that the jaws are located on opposite sides of the protruding tissues, (iv) thereafter closing the jaws to clamp the protruding tissues, and (v) subsequently operating the occlusion component to permanently constrict a portion of the protruding tissues.

Where the instrument assembly includes a shutter or closure member for covering the window, the inserting of the hollow body member into the body lumen typically includes inserting the hollow body member with the shutter or closure member covering the window, while the method further comprises moving the shutter or closure member to uncover the window to permit the organic tissues to protrude through the window.

The moving of the shutter or closure member may include sliding the shutter or closure member relative to the hollow body member.

The method may additionally comprise attaching the hollow body member to an insertion member of an endoscope, so that the inserting of the hollow body member into the body lumen includes inserting the endoscope with the hollow body member attached thereto into the body lumen.

Where the hollow body member has a channel and a chamber, the window communicating with the chamber, the attaching of the hollow body member to the insertion member includes inserting the endoscope insertion member into the channel of the hollow boy member, and the method further comprises visualizing the protruding tissues in the chamber via an optical system having access to the chamber.

The present invention offers to provide minimally invasive treatment of one or more hemorrhoids through an anal cannula having a normal size or any degree of enlargement and protrusion. The approach of the present invention recommends the application of a staple line in a transverse direction (in relation to the anal axis) above the so-called dentate line (the dentate line is an anatomical line in the anal canal, above which the mucosa is pain-insensitive). Since the C-curve of the tissue-occluding jaws in a closure device of the present invention is essentially a circular section, all the advantages of circular stapling can be attained in the present methodology without the disadvantages. A smaller stapling cartridge or jaws with a different C-curve (more or less curved) can be used for smaller hemorrhoids or different rectums as needed without the potential of rectal narrowing or substantial collateral ano-rectal trauma, which accompany the method of U.S. Pat. No. 6,142,933. The particular anal port or anoscope design of the present invention, together with the C-curved stapler clamp, allows treatment of the chosen number of hemorrhoids without incurring unnecessary surgical trauma and expense. The anoscope and tissue-occluding device of the present invention can be used in the office without the need for trained medical assistance. Less surgical trauma, particularly in the treatment of hemorrhoids, translates into a reduced loss of work and interruption of normal life.

BRIEF DESCRIPTION OF THE DRAWINGS

FIGS. 7A-7F are schematic cross-sectional views of the anoscope of FIG. 1 inserted into an anal canal, showing successive steps of a method in accordance with the present invention.

FIG. 15 is a top, rear, and left side perspective view of the tissue occluding anoscope of FIGS. 13 and 14.

FIG. 16 is a top, rear, and left side perspective view of the tissue occluding anoscope of FIGS. 13-15, in longitudinal or axial section.

DETAILED DESCRIPTION

Figure 1:
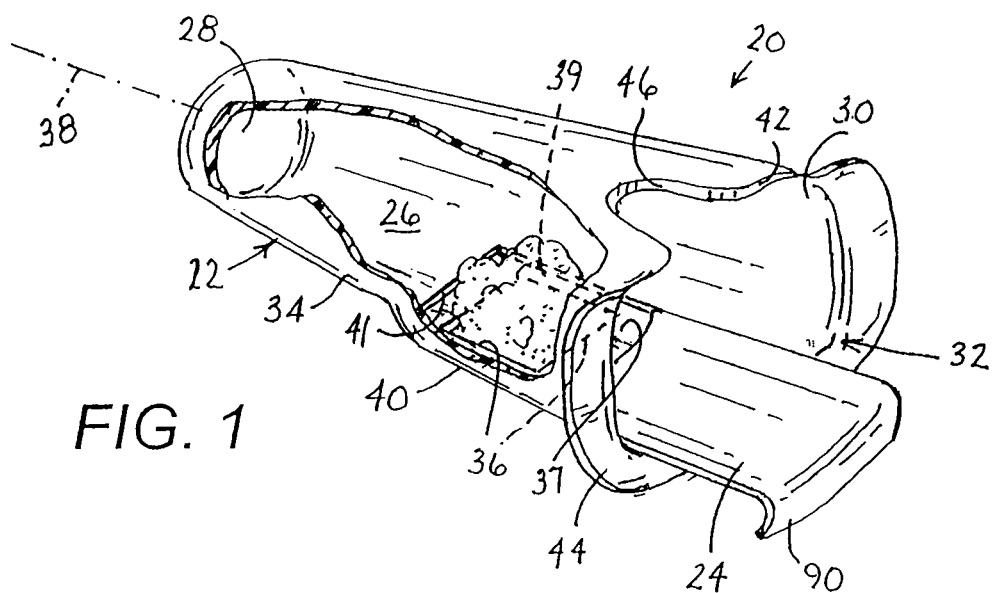
FIG. 1 is a schematic perspective view, partially broken away, of an anoscope in accordance with the present invention, for use in a method in accordance with the present invention, showing a pair of jaws.

As illustrated in FIG. 1, an anoscope 20 for hemorrhoidal surgery compromises a hollow body 22 and a shutter member 24. Hollow body 22 defines a longitudinal channel or lumen 26 that is closed at a distal end 28 and formed with an opening 30 at a proximal end 32. Opening 30 enables visual inspection of a surgical site and the insertion of instrumentation. Hollow body 22 has a sidewall 34 provided with a rectangular window 36 spaced from distal end 28 and preferably also from proximal end 28 of hollow body 22.

Shutter member 24 is movably mounted to hollow body 22 to cover window 36 during a positioning of anoscope 20 in an anal canal. Shutter member 24 is removable from window 36 to permit hemorrhoidal tissues to protrude through window 36 into anoscope channel 26. More specifically, shutter member 24 is slidably mounted to hollow body 22, is disposed in hollow body 22, and has a shape conforming to sidewall 34 in a region thereof about window 36.

Shutter member 24 is located in a track 37 in the hollow body. Track 37 takes the form of a shallow depression or recess with longitudinal edges or shoulders 39 serving as guides for the sliding shutter member 24. A transverse edge or shoulder 41 serves as an abutment to continued distal motion of shutter member 24 during an insertion stroke thereof. Shutter member 24 may be locked into track 37, for example, by grooves (not illustrated) in longitudinal edges or shoulders 39.

Figure 8:
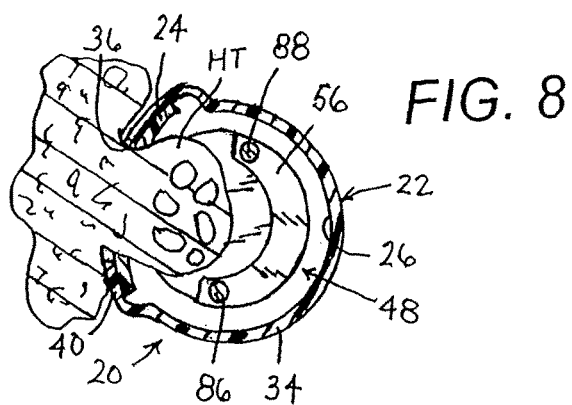
FIG. 8 is a schematic transverse cross-sectional view taken along line IX IX in FIG. 7D.
Figure 9:
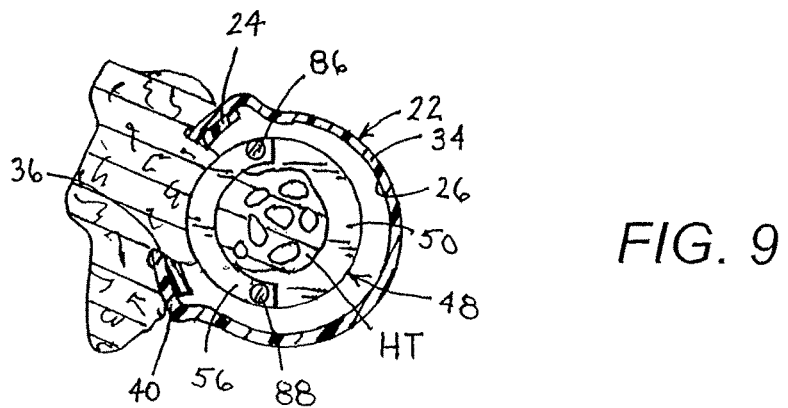
FIG. 9 is a schematic transverse cross-sectional view taken along line VIII-VIII in FIG. 7C.

Hollow body 22 generally has a longitudinal axis 38, and sidewall 34 is formed with a bulging portion or protrusion 40 located on one side of the axis and extending from proximal end 32 of the hollow anoscope body partially along a length of sidewall 34 towards distal end 28. Window 36 is located in bulging portion 40, and shutter member 24 is slidable along and in engagement with bulging portion 40. As shown in FIGS. 8, and 9, shutter member 24 and bulging portion 40 may be cooperatively formed so that the bulging portion serves as a track that slidably retains the shutter member. Window 36 may generally take any shape suitable for the admission of protruding hemorrhoidal tissues HT (FIGS. 7B-7F, 8, and 9). Rectangular and circular are possible shapes.

Hollow body 22 of anoscope 20 has a rim 42 surrounding opening 30 at proximal end 32. Hollow body 22 is preferably provided along rim 42 with a flange 44 serving as a stop for preventing anoscope 20 from slipping entirely into the anal canal. Hollow body 22 is further provided along rim 42 with a cutout 46 disposed on a side of axis 38 opposite bulging portion 40. Cutout 46 facilitates manipulation of any instrument that is inserted into anoscope 20 for operating on hemorrhoidal tissues. In addition, cutout 46 facilitates observation of window 36 and of hemorrhoidal tissues HT protruding into longitudinal channel 26 through window 36.

In some applications, window 36 may extend in a proximal direction all the way to flange 44. In any case, window 36 is large enough for the admission of hemorrhoids into channel or lumen 26 of anoscope 20. The placement of window 36 in bulging portion or protrusion 40 is conducive to providing window 36 with properly large dimensions.

Figure 2:
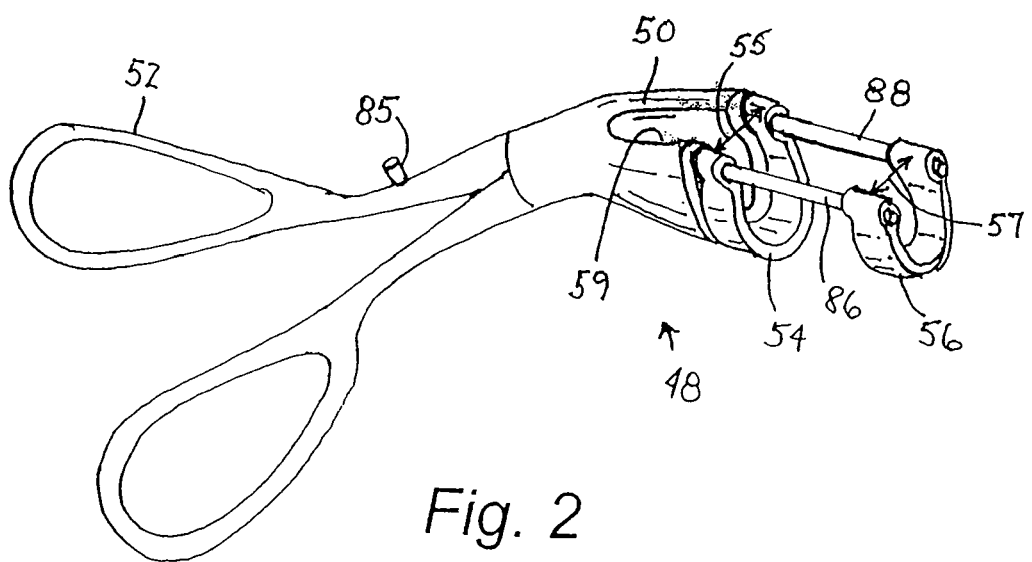
FIG. 2 is a schematic perspective view, partially broken away, of a tissue occlusion device in accordance with the present invention, for use in a method in accordance with the present invention.

Anoscope 20 may be provided as part of a surgical instrument assembly than also includes a hemorrhoid treatment device 48 depicted in FIG. 2. Device 48 comprises an instrument shaft 50, a handle or actuator 52 connected to the shaft at a proximal end thereof, and a pair of jaws 54 and 56 (proximal and distal) mounted to the shaft at a distal end thereof. Handle 52 is operatively connected to jaws 54 and 56 for alternatively opening and closing the jaws. Jaws 54 and 56 each takes the form of a C- or U-shaped clamping member movable alternately away from and towards the other jaw.

Jaws 54 and 56 define respective gaps 55 and 57. A distal end portion of instrument shaft 50 is U- or C-shaped in cross-section and defines a recess 59 aligned and communicating with gap 55. This asymmetrical shape of the distal end of instrument shaft 50 facilitates a visualization of a surgical site while a distal end portion of hemorrhoid treatment device 48 is inserted into anoscope 20.

Figure 3:
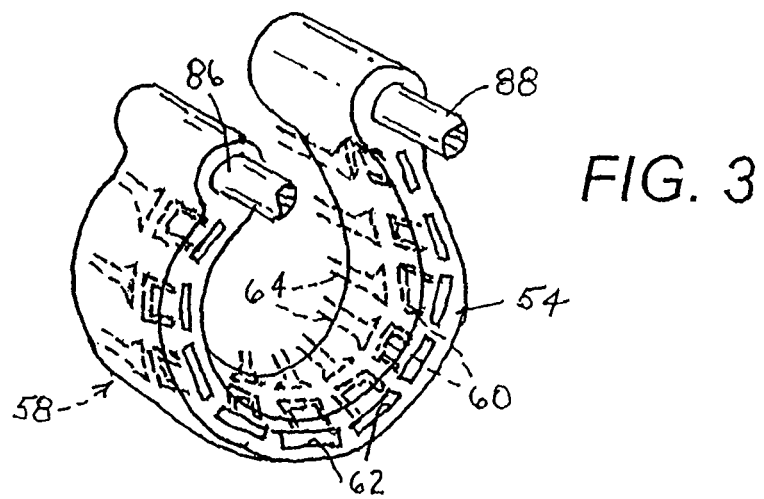
FIG. 3 is a schematic perspective view of a proximal one of the jaws depicted in FIG. 1, showing details of a tissue occlusion mechanism.

A hemorrhoid occlusion component is mounted to jaws 54 and 56 for acting on tissues gripped between the jaws, to couple the tissues to each other. The hemorrhoid occlusion component may take any form capable of bonding organic tissues, particularly hemorrhoidal tissues, to one another. As depicted in FIG. 3, the hemorrhoid occlusion component may take the form of a stapling mechanism 58 including a plurality of staples 60 disposed in an arcuate configuration inside proximal jaw 54. Staples 60 are longitudinally aligned on a distal side with respective ejection apertures 62 in jaw 54 and on a proximal side with respective pusher elements 64. Pusher elements 64 may be disposed on a proximal side in contact with a pressure application ring (not shown) or other force-transmission structure operatively connected at a proximal end with handle 52. Distal jaw 56 is provided with a series of anvil elements or areas (not shown) that are aligned with respective slots or ejection apertures 62, for causing staple closure upon firing.

Staples 60 may be housed in a disposable cartridge element that may be a portion or the entirely of proximal jaw 54. This variation permits a surgeon, proctologist or other medical practitioner to clamp plural hemorrhoids in the course of a single procedure. After the stapling of one hemorrhoid, as discussed below with reference to FIGS. 7A-7E, the empty cartridge (e.g., jaw 54) is removed and replaced with a similar loaded staple cartridge.

Figure 4:
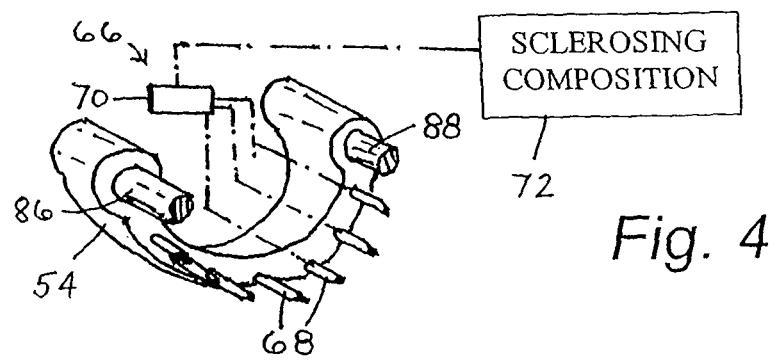
FIG. 4 is a schematic perspective view of the proximal jaw of FIG. 1, showing details of another tissue occlusion mechanism.

As illustrated in FIG. 4, an alternative hemorrhoid occlusion component takes the form of an injection mechanism 66 including a plurality of hollow needles 68 fixed to proximal jaw 54. Needles 68 are longitudinally oriented and circumferentially spaced about jaw 54. Needles 68 are connectable via a distribution manifold 70 to a reservoir 72 of a sclerosing composition such as a concentrated sugar solution or a biocompatible adhesive.

Figure 5:
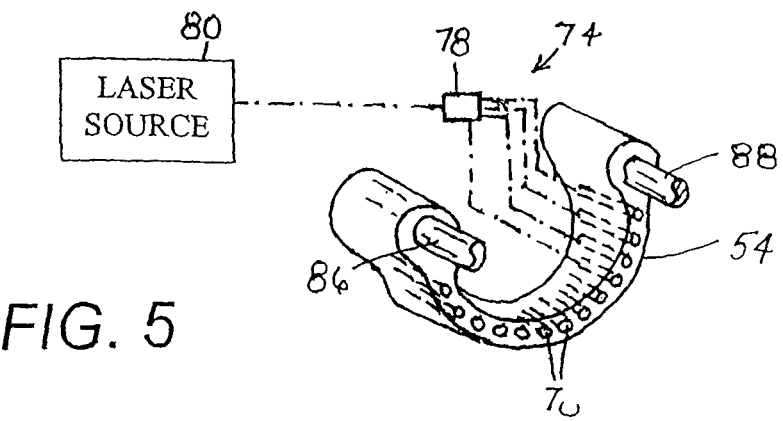
FIG. 5 is a schematic perspective view of the proximal jaw of FIG. 1, showing details of a further tissue occlusion mechanism.

FIG. 5 shows another alternative occlusion component in the form of a radiant-energy applicator 74, for instance, in the infrared or optical portions of the electromagnetic spectrum. More specifically, radiant-energy applicator 74 includes optical fibers 76 connectable via a distribution manifold 78 to a source 80 of laser radiation.

Figure 6:
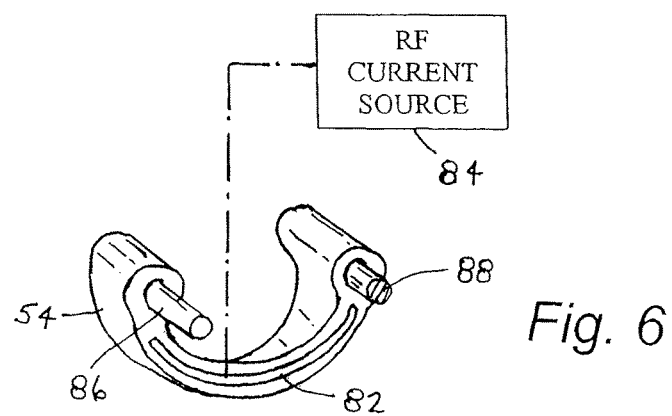
FIG. 6 is a schematic perspective view of the proximal jaw of FIG. 1, showing details of yet another tissue occlusion mechanism.

FIG. 6 depicts yet another alternative occlusion component in the form of an electrode 82 mounted to proximal jaw 54 and facing in the distal direction towards distal jaw 56. Distal jaw 56 may also be provided with an electrode (not shown), in the case of a bipolar delivery of electrical energy. Electrode 82 is connectable to a source 84 of radio-frequency current for delivering RF cauterizing current to hemorrhoidal tissues.

Jaws 54 and 56, together with rods 86 and 88, may form a disposable occlusion cartridge that is removable from shaft 50. Upon completion of a hemorrhoid treatment procedure on one patient, the cartridge is removed and replaced with a new cartridge for use on another patient.

In the case of injection mechanism 66, radiant-energy applicator 74, or electrode 82, handle 52 may be provided with a port or connector 85 for enabling the coupling of the hand-held hemorrhoid treatment device 48 to reservoir 72, laser source 80, or RF electric source 84, respectively.

As further illustrated in FIG. 2, jaws 54 and 56 are mounted to a pair of parallel rods 86 and 88 each connected at a proximal end to instrument shaft 50. Jaws 54 and 56 are connected to one another and to shaft 50 via rods 86 and 88 so that the jaws remain parallel to one another and perpendicular to rods 86 and 88 during opening and closing strokes of the jaws. Any reciprocatable drive mechanism known in the art or hereafter developed may be operatively coupled to jaws 54 and 56 and handle 52 for enabling opening and closing of jaws 54 and 56 by manipulation of handle 52.

In the embodiment of the hemorrhoid treatment device 48 shown in FIG. 2, distal jaw 56 is slidably coupled to rods 86 and 88, proximal jaw 54 is fixed with respect to the rods, and the rods are coupled to distal jaw 56 on opposite sides thereof. Jaws 54 and 56 and rods 86 and 88 may be manufactured as a disposable cartridge assembly detachable from instrument shaft 50. Alternatively, the operative components, such as staples 60 and apertures 62, may be formed as parts of a disposable cartridge separate from the jaws 54 and 56.

Figures 7A, 7B:
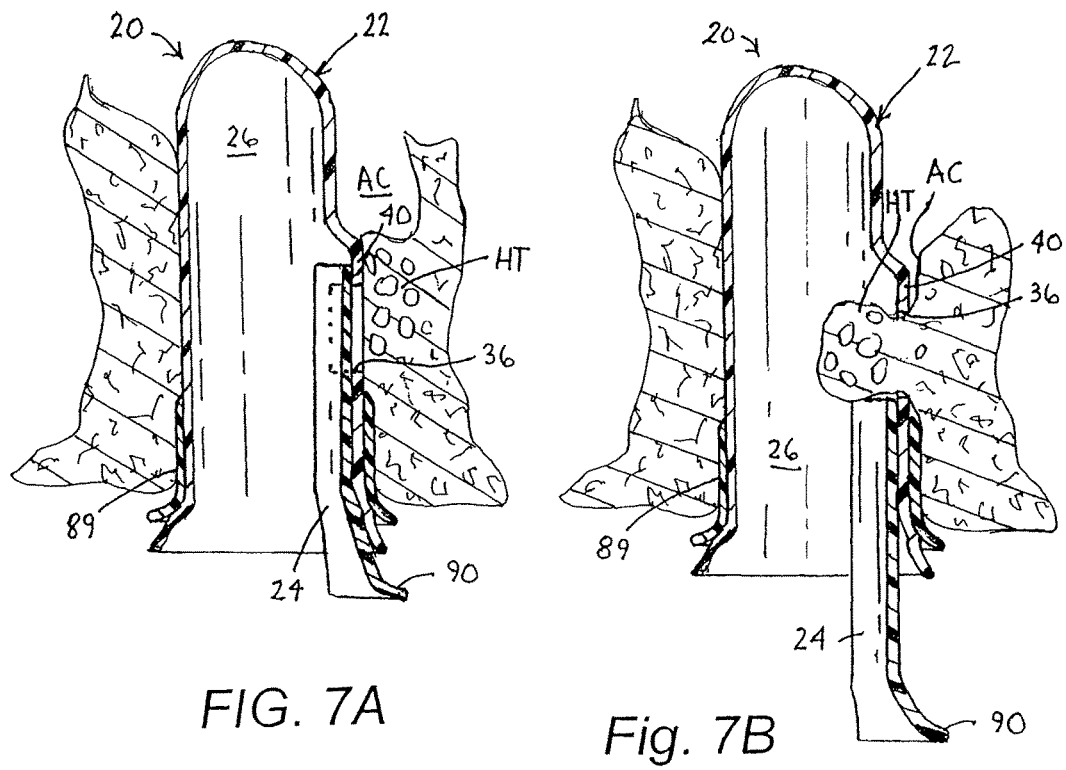

FIGS. 7A-7F illustrate steps in a method for the treatment of hemorrhoids utilizing anoscope 20 and hemorrhoid treatment device 48. As shown in FIG. 7A, anoscope 20 with shutter member 24 closing window 36 is inserted through a transparent anal port member 89 into an anal canal AC and is manipulated so that hemorrhoidal tissues HT are disposed adjacent to window 36. This procedure may involve longitudinally shifting and/or rotating the anoscope 20 inside the anal canal AC until the anoscope is in the desired position relative to the hemorrhoidal tissues HT. To that end, shutter member 24 and optionally sidewall 34 of hollow body 22 are made of a transparent polymeric material. Thus, anal tissues can be visualized through sidewall 34 and shutter member 24 during the manipulation of anoscope.

Figure 7C:
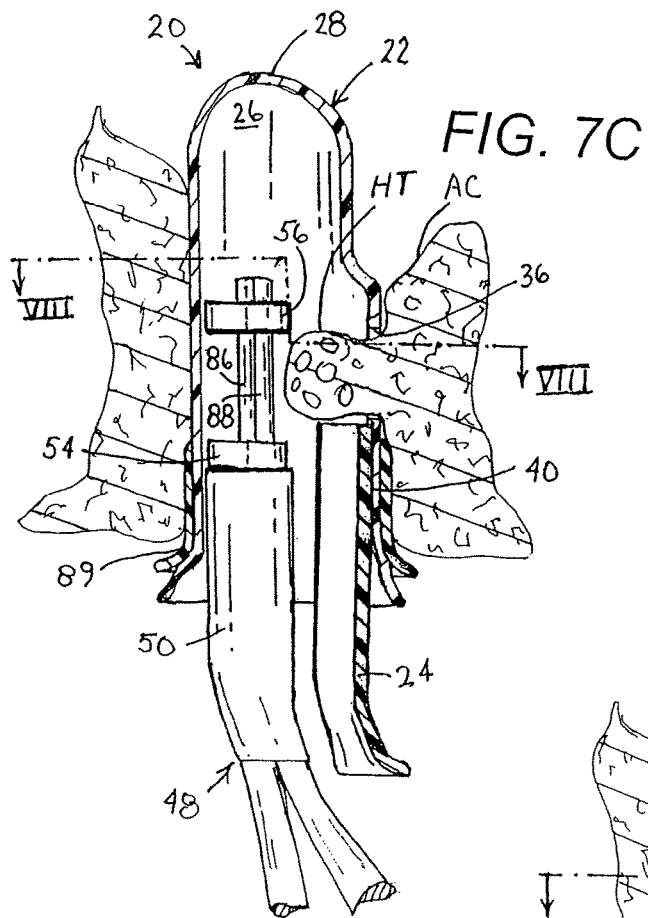
Figure 7D:
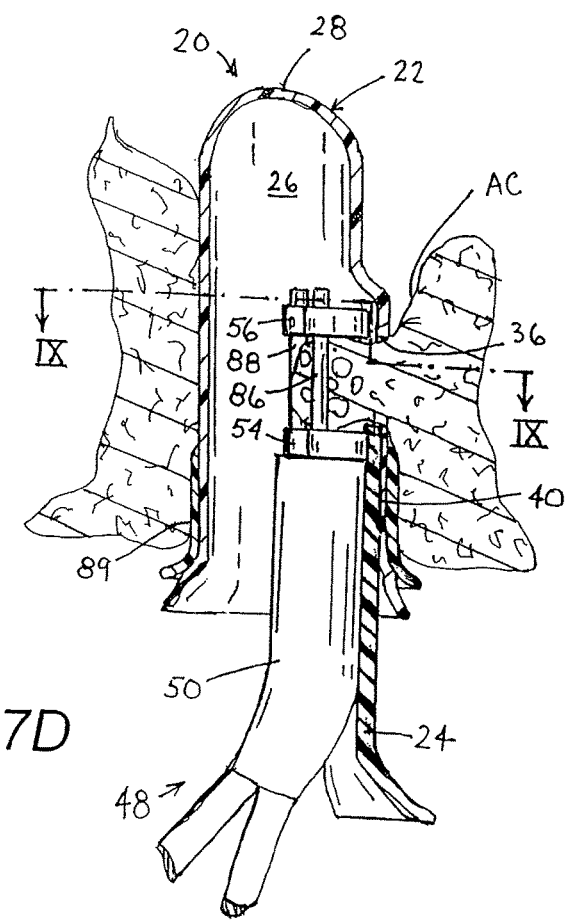

Upon an appropriate positioning of anoscope 20, shutter member 24 is grasped at an external flange or finger grip 90 and pulled in a proximal direction, as indicated by an arrow 92 in FIG. 7B. This action uncovers window 36 and enables hemorrhoidal tissues HT to protrude through the window into channel 26 of anoscope 20. Subsequently, a distal end portion of hemorrhoid treatment device 48 particularly including jaws 54 and 56 is inserted into anoscope 20. As depicted in FIG. 7C, this insertion may be performed with jaw 54 and 56 located in channel 26 on a side of longitudinal axis 38 opposite bulging sidewall portion 40 (see FIGS. 7C and 8), whereby the protruding hemorrhoidal tissues HT pass through a slot or gap 94 defined by jaw 56. In that case, after the placement of hemorrhoid treatment device 48, the device is rotated about a longitudinal axis and possibly translated orthogonally to that axis to align jaws 54 and 56 with a neck or base region 96 of the protruding hemorrhoidal tissues HT as shown in FIGS. 7D and 9.

In an alternative deployment procedure, the distal end portion of hemorrhoid treatment device 48 is inserted into anoscope 20 in such a manner that jaws 54 and 56 are located in channel 26 on the same side of longitudinal axis 38 as bulging sidewall portion 40 (see FIGS. 7C and 8). Because the protruding hemorrhoidal tissues HT are malleable, distal jaw 56 of hemorrhoid treatment device 48 may be slipped past the protruding tissues. It may be necessary or expedient to wiggle hemorrhoid treatment device 48 during the insertion (and removal) phase of a deployment operation, depending on the relative sizes of anoscope 20, hemorrhoid treatment device 48, and the protruding hemorrhoidal tissues HT. In this alterantive deployment procedure, there is no need to rotate device 48 about a longitudinal axis to align jaws 54 and 56 with a neck or base region 96 of the protruding hemorrhoidal tissues HT as shown in FIGS. 7D and 9.

With jaws 54 and 56 located on opposite sides of hemorrhoidal tissues HT, the are approximated, as depicted in FIG. 7E, to clamp the hemorrhoidal tissues HT. Preferably, jaws 54 and 56 are maintained in parallel to one another during their closing and opening strokes.

While jaws 54 and 56 are clamped about neck region 96 of tissues HT as shown in FIG. 7E, the tissue occlusion component (FIGS. 3-6) of the hemorrhoid treatment device 48 is operated to permanently constrict hemorrhoidal tissues HT in or about neck region 96. In the case of stapling mechanism 58 (FIG. 3), staples 60 are fired through ejection apertures 62 in jaw 54 by a distal motion of pusher elements 64, the staples being closed upon meeting respective anvil elements (not illustrated) in distal jaw 56. In the case of injection mechanism 66 (FIG. 4), hollow needles 68 fixed to proximal jaw 54 are naturally or automatically inserted into hemorrhoidal tissues during the approximation of jaws 54 and 56. Sclerosing composition is then guided from reservoir 72 into the hemorrhoidal tissues HT. In the case of radiant-energy applicator 74 (FIG. 5), the applicator is operated to generate electromagnetic radiation of a predetermined spectral range, which is then directed into hemorrhoidal tissues HT via optical fibers 76. In the case of the RF-cautery componentry of FIG. 6, radio-frequency current is conducted from source 84 through electrode 82 into hemorrhoidal tissues HT. Where distal electrode 56 is also provided with an electrode, the current passes from electrode 82 through neck or base region 96 to jaw 56. In the case of a monopolar cauterization current, the current spread out from tissues HT into the patient's body.

After the occlusion operation has been performed, handle 52 is operated to separate jaws 54 and 56 from one another and the treatment device 48 is manipulated to separate the jaws from the treated hemorrhoidal tissues HT (FIG. 7F). Treatment device 48 is then further manipulated to withdraw it from anoscope 20. Again, because of the deformability of the clamped hemorrhoidal tissues HT, in many cases it will be possible to simply withdraw the hemorrhoid treatment device 48 without rotation, but perhaps with some wiggling.

The hemorrhoidal tissues HT distal to the occluded neck region 96 may be transected with a scalpel or allowed to ischemically regress or self amputate. Self-amputation occurs within a few days of the occlusion procedure. Ischemic regression takes place within several weeks. Ischemic regression and self-amputation are the result of occlusion of bloods vessels in neck or base region 96.

Bulging portion or protrusion 40 of anoscope 20 serves as a retractor of collateral anal or rectal tissues. In addition, bulging portion or protrusion 40 creates more work space in the area of hemorrhoidal tissues HT. This design allows for better access to the neck or base 96 of tissues HT, which is located in the submucosal layer close to the rectal muscle.

Figure 10:
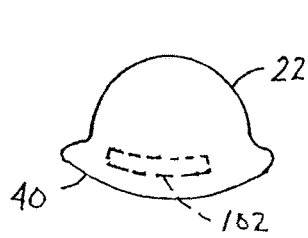
FIG. 10 is a diagrammatic transverse cross-section of the anoscope of FIGS. 1 and 7A-7F.
Figure 11:
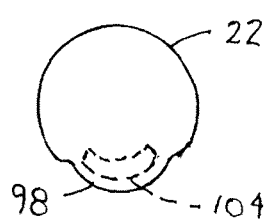
FIG. 11 is a diagrammatic transverse cross-section similar to FIG. 10, showing an alternative design of the anoscope of FIGS. 1 and 7A-7F.
Figure 12:
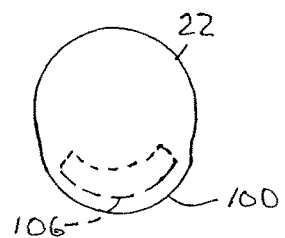
FIG. 12 is a diagrammatic transverse cross-section similar to FIG. 10, showing another alternative design of the anoscope of FIGS. 1 and 7A-7F.
Figure 13:
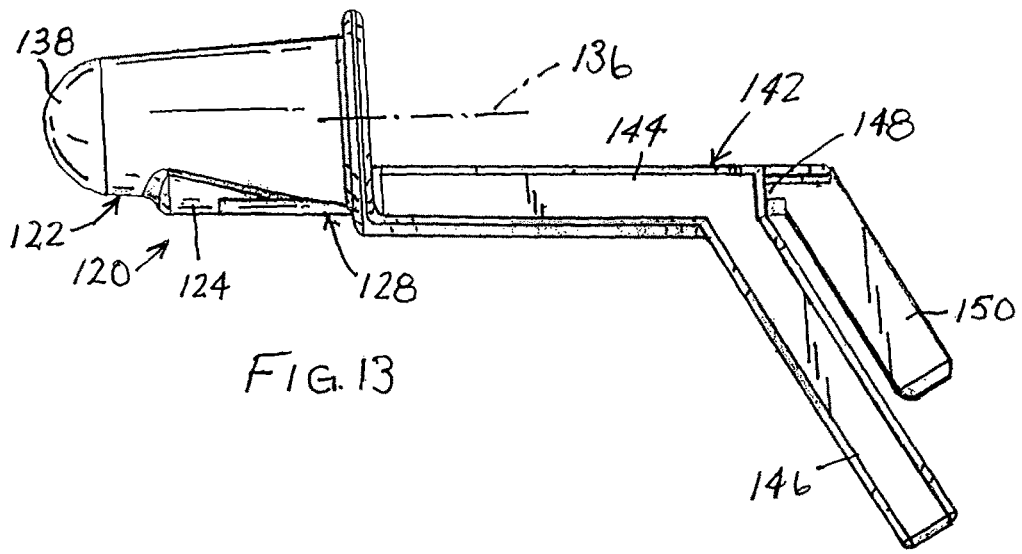
FIG. 13 is a side elevational view of an anoscope with an included tissue occlusion component, in accordance with the present invention.
Figure 14:
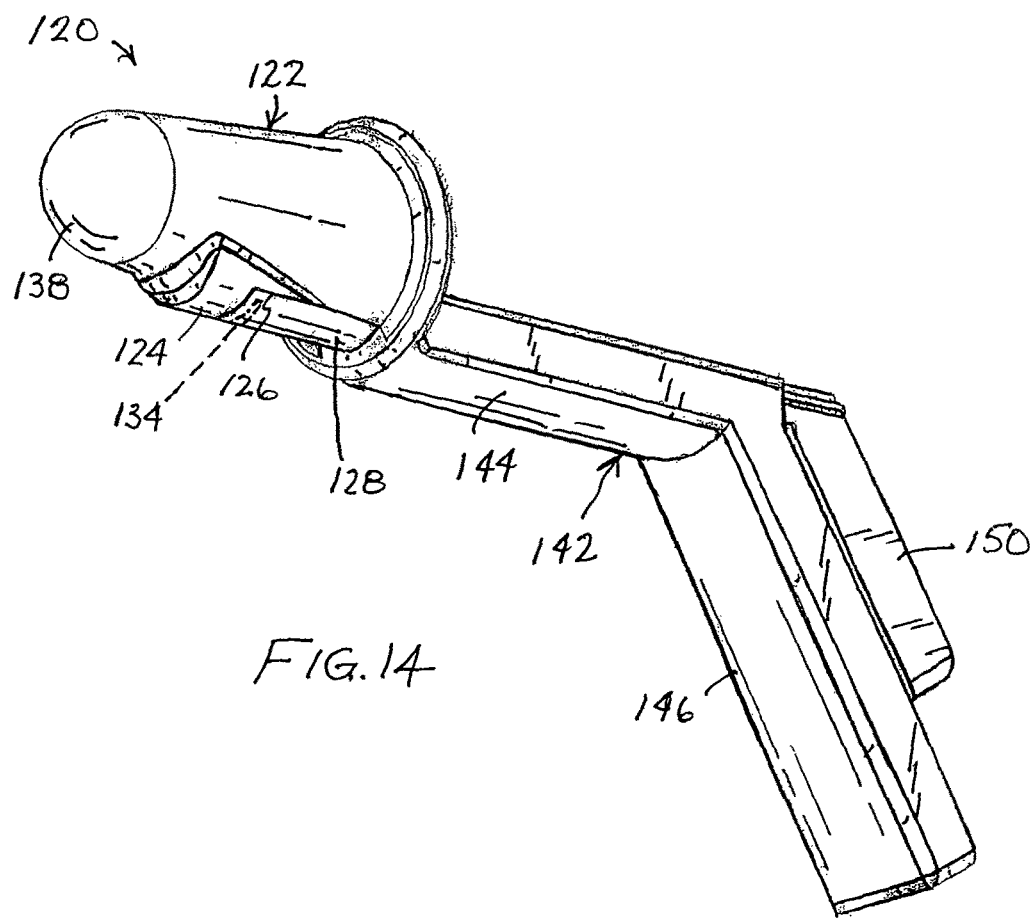
FIG. 14 is a bottom, front and left side perspective view of the tissue occluding anoscope of FIG. 13.

FIGS. 8-10 show one configuration of bulging portion or protrusion 40, where the protrusion has a radius of curvature that is greater than a radius of curvature of the remaining part of hollow body 22. Other configurations are possible. FIG. 11 depicts a configuration where a bulging portion or protrusion 98 has a radius of curvature that is smaller than the radius of curvature of the main part of hollow body member 22. FIG. 12 illustrates a configuration where a bulging portion or protrusion 100 has a radius of curvature that is essentially equal to the radius of curvature of the main part of hollow body member 22. The dashed lines 102, 104, 106 represent the respective occluding jaws of hemorrhoid treatment device 48.

Generally, the manipulating of anoscope 20 to align window 36 with hemorrhoidal tissues is performed after the inserting of anoscope 20 into the anal canal. Anoscope 20 and port member 89 are preferably made of a transparent polymeric material that facilitates visual inspection and locating of the hemorrhoids. Jaws 54 and 56 of the occlusion device are inserted into anoscope 20 after the inserting of anoscope 20 into the anal canal AC, after the manipulating of anoscope 20 to align window 36 with hemorrhoidal tissues HT, and after the protruding of the hemorrhoidal tissues HT through window 36.

A hemorrhoid treatment instrument or device as disclosed hereinabove may be partially or completely disposable. Where both jaws 54 and 56 are parts of a disposable cartridge removably attached to shaft 50, the proximal portion of the instrument may be utilizable in treating different patients at different times. Alternatively or additionally, where proximal jaw 54 contains a staple magazine, jaw 54 may be replaceable to permit multiple hemorrhoid occlusion procedures on the same patient.

Figure 17:
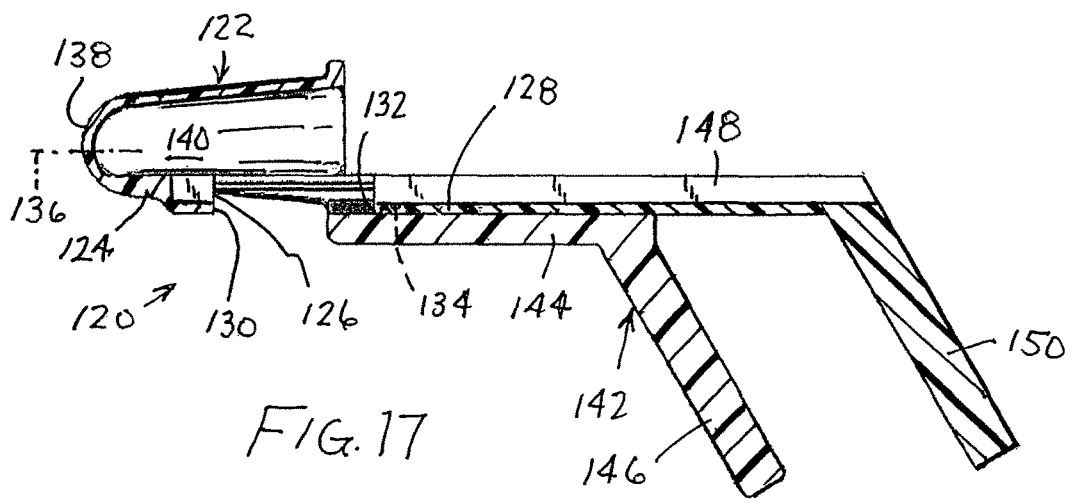
FIG. 17 is a longitudinal cross-sectional view of the tissue occluding anodsocpe of FIGS. 13-16, showing a shutter or closure member in an open or tissue receiving position.
Figure 18:
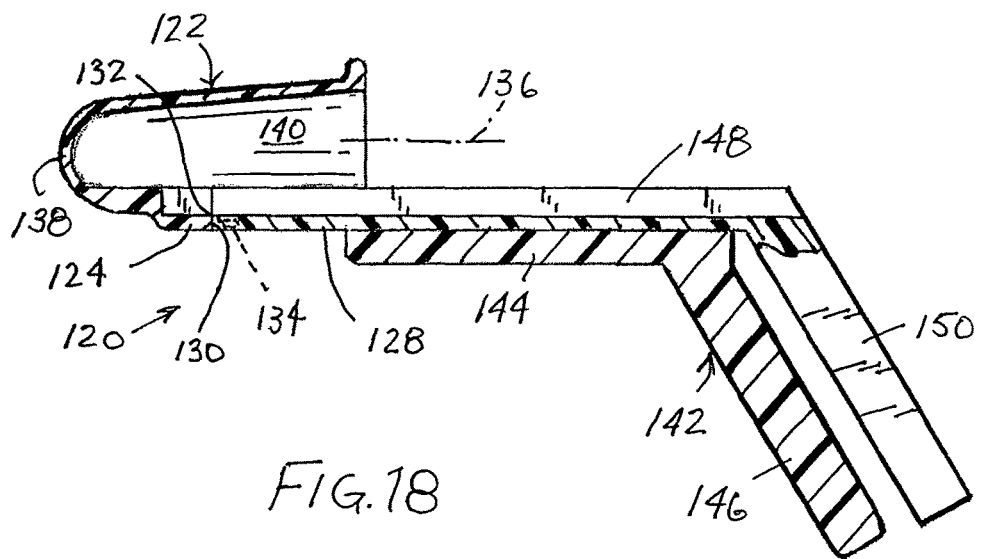
FIG. 18 is a view similar to FIG. 17, showing the shutter or closure member in a closed or unclamping position.
Figure 19:
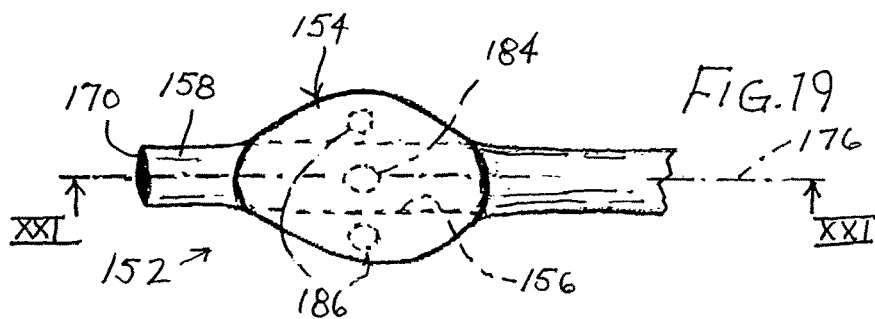
FIG. 19 is a schematic top plan view of an embodiment of an endoscopic tissue occlusion assembly in accordance with the present invention.
Figure 20:
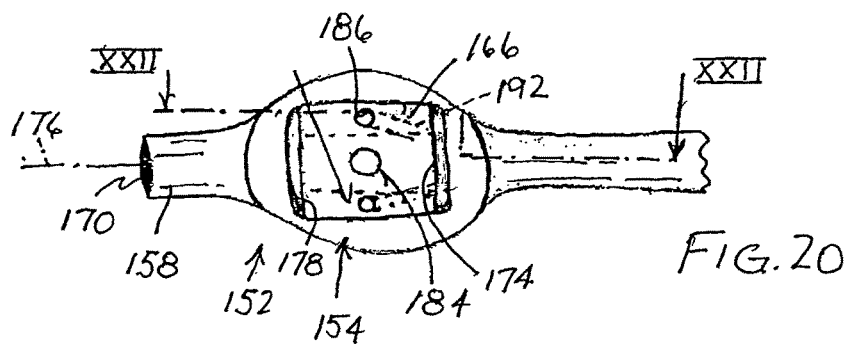
FIG. 20 is a schematic bottom view of the endoscopic tissue occlusion assembly of FIG. 19.
Figure 21:
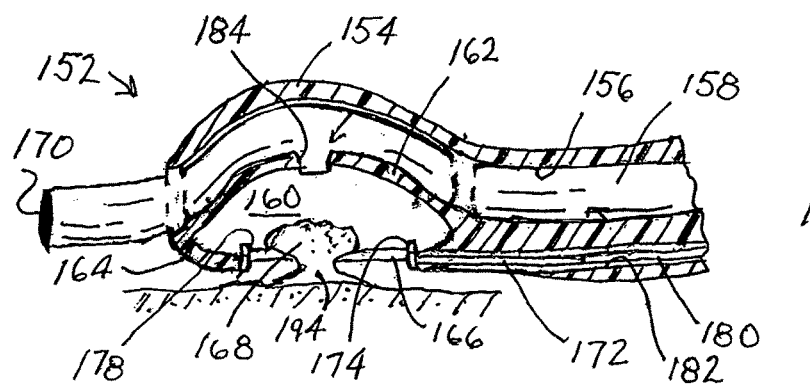
FIG. 21 is a schematic longitudinal cross-sectional view of the tissue occlusion assembly of FIGS. 19 and 20, taken along line XXI-XXI in FIG. 19.
Figure 22:
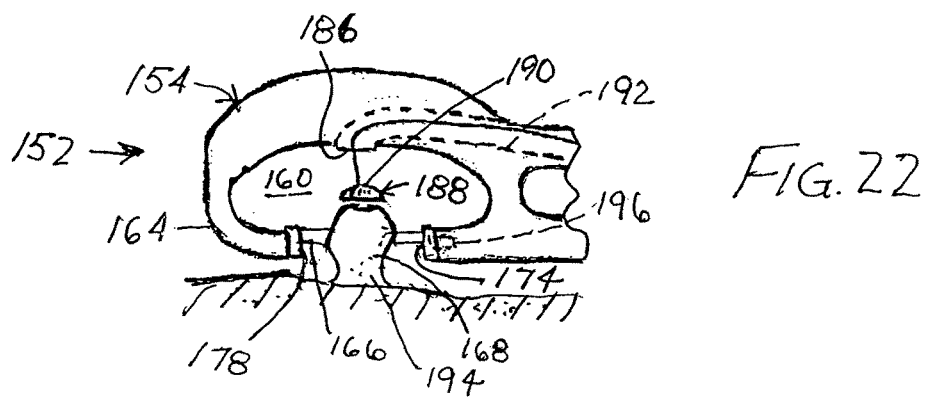
FIG. 22 is a schematic cross sectional view of the tissue occlusion assembly of FIGS. 19-21, taken along line XXII-XXII in FIG. 20.

FIGS. 13-18 depict a surgical instrument assembly and more particularly a tissue-occluding anoscope assembly 120 for the treatment of hemorrhoids. The instrument assembly 120 comprises a hollow member 122 having a sidewall 124 provided with a window 126 and further comprises a closure member 128 slidably connected to the hollow member for alternately covering and uncovering the window. Hollow member 122 has a first clamping surface 130 along an edge of window 126. Closure member 128 has a second clamping surface 132 opposing clamping surface 130 and disposable substantially adjacent thereto in a clamping or closure configuration of the instrument shown in FIGS. 13-15 and 18. Closure member 128 is slidable in a proximal direction, away from clamping surface 130 to open window 126, as shown in FIGS. 16 and 17.

Tissue occluding instrument assembly 120 additionally comprises a tissue occlusion component 134 mounted to at least one of the hollow member 122 and the closure member 128 for acting on organic tissues gripped between clamping surfaces 130 and 132, to couple the tissues to each other. Tissue occlusion component 134 may be a stapling mechanism, an injection mechanism connectable to a reservoir of a sclerosing composition, or optical fibers connectable to a source of laser radiation.

Sidewall 124 of hollow member 122 is generally conically curved, so that clamping surfaces 130 and 132 have a curved form, e.g., a C shape or U shape. Clamping surfaces 130 and 132 lie in parallel planes that extend perpendicularly to a longitudinal axis 136 of instrument 120 and remain parallel to one another during opening and closing strokes of closure member 128. Closure member 128 moves parallel to axis 136.

Hollow member 122 is closed at a distal end 138 and defines a longitudinal channel 140 in which closure member 128 is disposed in part. Window 126 communicates with channel 140. At a proximal end, opposite closed end 138, hollow body 122 is provided with a handle 142 including a extending longitudinally stem 144 (that is oriented at a small angle relative to axis 136) and a substantially transversely extending handgrip 146. Closure member 128 includes a main part 148 formed as a channel member and, at an end of main part 148 opposite clamping surface 132, a handgrip 150 extending parallel to handgrip 146 of handle 142. Stem portion 144 of handle 142 is formed as a channel member that slidingly receiving main part 148 of closure or shutter member 128.

FIGS. 19-22 depict an endoscopic version of a tissue occluding instrument assembly 152 including a hollow body member 154 that has a channel 156 for receiving an insertion member 158 of an endoscope. Hollow member 154 incorporates a chamber 160 that is located laterally relative to channel 156. Chamber 160 is optionally separated from channel 156 by a partition or wall 162. Endoscope insertion member 158 extends in an arc about chamber 160, which is accordingly located in a bulging portion 164 of hollow body member 154.

Hollow body member 154 and particularly bulging wall 164 thereof is provided with a window or aperture 166 through which organic tissues such as a polyp 168 may protrude during an endoscopic tissue occluding procedure. During such a procedure, endoscope insertion member 158, with hollow body member 154 attached thereto as illustrated, is inserted through a natural body opening such as the anal orifice into an internal lumen such as the colon. Optical components (not illustrated) in the distal end face 170 of endoscope insertion member 158 are used to visually inspect the walls of the body lumen and to detect a surgical site containing polyp 168 or other undesirable tissue mass.

Tissue occluding instrument assembly 152 further includes a closure or shutter member 172 that includes a tissue clamping surface 174 at a distal end. Surface 174 generally has an arcuate shape and lies in a plane transverse to a longitudinal axis 176 of the instrument assembly. Surface 174 is opposable to another arcuate tissue clamping surface 178 that is attached to hollow body member 154 along a distal edge (not separately labeled) of window 166. Surface 178 also lies in a plane transverse to a longitudinal axis 176 and is accordingly parallel to surface 174.

Closure or shutter member 172 is attached to a distal end of a rod 180 that is slidably disposed in a channel 182 of hollow body member 154 that extends parallel to axis 176. During an initial phase of a deployment operation, rod 180 is pushed in a distal direction so that closure or shutter member 172 covers or closes opening 166. Upon the reaching of a contemplated surgical site, rod 180 is pulled in a proximal direction to remove closure or shutter member 172 from window 166 and allow polyp 168 to protrude through window 166 into chamber 160.

Body member 154 is provided in chamber 160 with an opening 184 via which a visual inspection of chamber 160 may be undertaken. Opening 184 may provide visual access to chamber 160 via optical components of endoscope insertion member 158 (exemplarily including an illumination source, a lens, and an optical fiber bundle—none illustrated). Alternatively, as discussed hereinafter with reference to FIGS. 23 and 24, hollow body member 154 may be provided with its own dedicated optical components for establishing visual access to chamber 160.

Hollow body member 154 may additionally be provided along chamber 160 with openings 186 for enabling access to chamber 160 by the working tips of endoscopic instruments such as a suction device 188. Suction device 188 includes a conical head 190 that engages polyp 168. Upon an application of suction, device 188 is pulled in proximal direction through a working channel 192 of endoscope insertion member or hollow body member 154. Thus, polyp 168 is stretched out to facilitate an occlusion operation in which closure or shutter member 172 is moved in the distal direction so that pedicle or neck tissues 194 of polyp 168 are sandwiched between clamping surfaces 174 and 178. Occlusion componentry 196 then operates through clamping surface 178 and/or surface 176 to effectuate an occlusion of the pedicle or neck tissues 194. Occlusion componentry 196 exemplarily takes the form of a stapling mechanism, an injection mechanism connectable to a reservoir of a sclerosing composition, or optical fibers connectable to a source of laser radiation. In any of the embodiments of a tissue occluding instrument assembly disclosed herein, the tissue occluding componentry may effectuate a heating of the tissues via resistive heat producing elements or electrical current transmission components.

At the termination of the procedure discussed above with reference to FIGS. 19-22 as in other procedures contemplated herein, closure or shutter member 172 is opened after the application of the occlusion energy. The occluded tissue mass, e.g., polyp 168, is then allowed to slip out of chamber 160 back into the natural body lumen.

Figure 23:
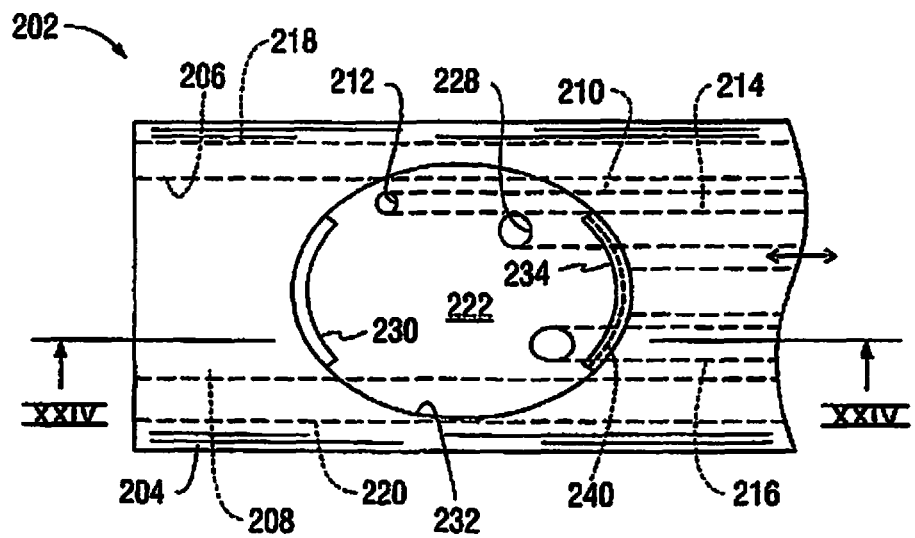
FIG. 23. is a schematic bottom view of another embodiment of an endoscopic tissue occlusion assembly in accordance with the present invention.
Figure 24:
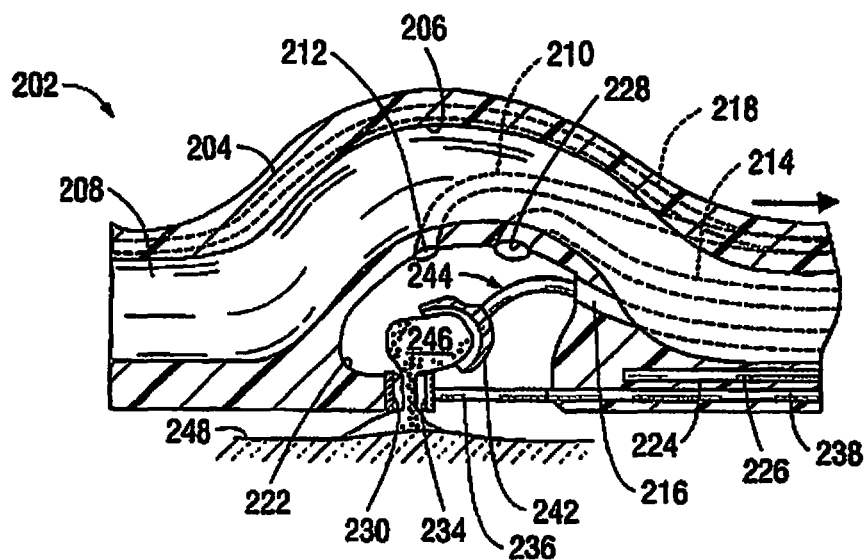
FIG. 24 is a schematic longitudinal cross-sectional view of the tissue occlusion assembly of FIG. 23, taken along line XXIV-XXIV in FIG. 23.
Figure 25:
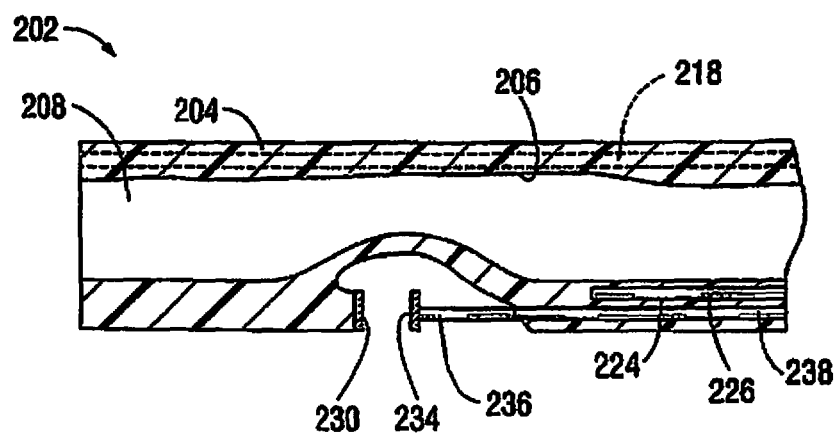
FIG. 25 is a schematic longitudinal cross-sectional view similar to FIG. 24 prior to formation of the expanded chamber.

FIGS. 23 and 24 depict a tissue occluding instrument assembly 202 similar to instrument assembly 152 of FIGS. 19-22. In assembly 202, a hollow body member 204 having a channel 206 receiving an endoscope insertion member 208 incorporates a fiber-optic illumination guide 210, a fiber-optic image guide 214, at least one working channel 216 for the deployment of endsocopic instrument, cables 218 and 220 for assisting in curving endoscope insertion member 208 to form a chamber 222 adjacent 206 as can be appreciated by comparing FIGS. 24 and 25. A stiffening rod 224 may be insertable through a channel 226 of hollow body member 204 also for purposes of assisting the formation of chamber 222.

Thus, hollow body member 204 may take the form of an endoscope sheath that is deformable at a distal end to expand chamber 222 from a collapsed insertion configuration to an expanded use configuration as shown particularly in FIG. 24. Illumination guide 210 and image guide 214 terminate distally at light access openings 212 and 228 along the wall of chamber 222.

A first arcuate clamping surface 230 is located on hollow body member 204, along a distal edge of a window 232 that communicates with chamber 222. A second arcuate clamping surface 234 is attached to the distal end of a closure or shutter member 236. Closure or shutter member 236 is connected to a rod 238 that moves the closure member alternately in a distal and proximal direction for effectuating a closure of window 232 during an insertion operation, an opening of window 232 to enable a protruding of a tissue mass into chamber 222, and a clamping of the protruding tissues during an application of energy to the tissues to effectuate an occlusion thereof. Tissue occluding componentry 240 provided on closure member 236 at surface 234 may take the form of any of the instrumentalities discussed above.

A suction head 242 of a suction device 244 inserted through working channel 216 may be used to draw a polyp 246 away from a wall 248 of a body lumen to facilitate a tissue occluding operation.

Tissue occluding instrument assemblies 152 and 202 may be used to treat a variety of pathologies (polyp, wall perforation, bleeding point at a previously placed staple line, etc.) but are generally not useful for treating hemorrhoids. Endoluminal tissue occluding instrument assemblies 152 and 202 may be used for treatment of lesions in natural and artificial lumens other than the colon, including the trachea, the bronchi, blood vessels (arteries and veins), etc.

Other known types of surgical maneuvers/operations can be performed using tissue occluding instrument assemblies 152 and 202, such as operating on an intimaVendothelial lesion in a vessel (arterial plaque, etc.) or operating on diseased venous or arterial valves. To carry out such additional procedures, a wide range of endoscopic surgical instruments (scissors, grasper, dissector, clip applier, etc.) can be introduced via endoscopic sheath channels 192, 216 to the targeted tissues.

Where organic tissues are to be severed and then extracted from the patient, the extraction may be implemented either via working channels 192, 216 or upon the withdrawal of the entire instrument. In the latter case, the severed specimen is carried in the chamber 160, 222 until outside of the patient.

Where a surgical operation results in a bleeding vessel, the vessel can be coagulated with RF or injected with sclerosing or hemostatic agent.

Any diagnostic and surgical maneuvers described here can be performed in conjunction with external maneuvers, for example, laparoscopic maneuvers. This laparo-endoluminal approach is generally known in the field of surgery and may facilitate the performance and safety of the operation while preserving the benefits of minimally-invasive approach. Although the invention has been described in terms of particular embodiments and applications, one of ordinary skill in the art, in light of this teaching, can generate additional embodiments and modifications without departing from the spirit of or exceeding the scope of the claimed invention. For example, rods 86 and 88 may be fixed to distal jaw 56 and slidably connected to shaft 50. Alternatively, rods 86 and 88 may be fixed to both distal jaw 56 and shaft 50, in which case proximal jaw 54 is slidable along rods 86 and 88 alternately towards and away from jaw 56. Also, more than two rods 86 and 88 may be provided for coupling distal jaw 56 to instrument shaft 50.

In yet another alternative design, both jaws 54 and 56 are movable along rods 86 and 88 during a clamping or closure stroke. Such a design facilitates hemorrhoid occlusion without tearing of the tissues below the occluded tissue base. If only one jaw 54 or 56 is movable along rods 86 and 88, then the entire instrument could be moved relative to the patient during closure of the jaws to ensure against undesired tissue tears. Where the distal jaw 56 is slidable along rods 86 and 88, the entire instrument is pushed into the patient while the distal jaw is moving in a proximal direction.

Accordingly, it is to be understood that the drawings and descriptions herein are proffered by way of example to facilitate comprehension of the invention and should not be construed to limit the scope thereof.

What is claimed is:

1. A method of treating tissue comprising:
   inserting into a body of a patient an endoscopic instrument having an expandable chamber in a collapsed configuration, the chamber having a distal portion, a proximal portion and an intermediate portion between the distal and proximal portions;
   after the insertion of the endoscopic instrument into the patient, expanding the chamber from the collapsed configuration to an expanded configuration to increase a transverse dimension of the chamber at the intermediate portion providing a larger space inside the chamber;
   inserting a distal portion of a working instrument into the chamber, the working instrument extending through a first channel in the endoscopic instrument, and the distal portion of the working instrument extending laterally with respect to a longitudinal axis of the endoscopic instrument; and
   visualizing the distal portion of the working instrument by a visualization device which extends through a portion of the endoscopic instrument and is separate and radially spaced from the first channel.

2. The method according to claim 1, wherein the step of expanding the chamber expands the chamber to only one side of the longitudinal axis of the endoscopic instrument.

3. The method of claim 1, wherein the visualization device terminates distally at an opening adjacent the chamber.

4. The method according to claim 1, wherein the step of visualizing the distal portion of the working instrument includes the step of angling the visualization device so it extends laterally with respect to the longitudinal axis of the endoscopic instrument.

5. The method according to claim 1, further comprising the steps of severing a tissue mass positioned within the chamber and removing the severed tissue mass from the patient by at least one of (i) removing the severed tissue mass via the first channel or (ii) removing the severed tissue mass by retaining the severed tissue mass in the chamber and withdrawing the endoscopic instrument from the patient.

6. The method according to claim 1, further comprising the step of receiving a polyp within the chamber and severing the polyp from the body utilizing the working instrument inserted through the first channel of the endoscopic instrument.

7. The method according to claim 1, further comprising the step of illuminating at least one portion of the chamber or tissue provided at or protruding into the chamber to enable a visual inspection thereof.

8. A method of treating tissue comprising:
inserting into a body of a patient an endoscopic instrument having an expandable chamber in a collapsed configuration, the endoscopic instrument further having a stiffening rod positionable proximal of the chamber, the stiffening rod movable with respect to the chamber to assist formation of the chamber;
after the insertion of the endoscopic instrument into the patient, expanding the chamber from the collapsed configuration to an expanded configuration to increase a transverse dimension of the chamber providing a larger space inside the chamber;
inserting a distal portion of a working instrument into the chamber, the working instrument extending through a first channel in the endoscopic instrument, and the distal portion of the working instrument extending laterally with respect to a longitudinal axis of the endoscopic instrument; and
visualizing the distal portion of the working instrument by a visualization device which extends through a portion of the endoscopic instrument and is separate and radially spaced from the first channel.

9. The method according to claim 8, wherein the chamber has a distal portion, a proximal portion and an intermediate portion between the distal and proximal portions, and the intermediate portion is expandable.

10. The method according to claim 9, wherein the step of expanding the chamber expands the chamber to only one side of the longitudinal axis of the endoscopic instrument.

11. The method according to claim 8, further comprising the steps of severing a tissue mass positioned within the chamber and removing the severed tissue mass from the patient by at least one of (i) removing the severed tissue mass via the first channel or (ii) removing the severed tissue mass by retaining the severed tissue mass in the chamber and withdrawing the endoscopic instrument from the patient.

12. The method according to claim 8, further comprising the step of illuminating at least one portion of the chamber or tissue provided at or protruding into the chamber to enable a visual inspection thereof.

13. A method of endoscopic surgery comprising the steps of:
providing an endoscopic instrument having a first channel, a separate second channel, a third channel and an expandable chamber at a distal portion of the endoscopic instrument, the first channel radially spaced from the second channel, the third channel having a stiffening member therein to assist formation of the chamber;
inserting the endoscopic instrument within a body lumen with the chamber in a collapsed position;
expanding the chamber to increase a transverse dimension of the chamber, the expanded chamber expanding laterally relative to the first channel;
visualizing the chamber by a visualization device inserted through the second channel, the second channel having an opening to the chamber; and
treating tissue within the expanded chamber by a working instrument extending through the first channel, the working instrument having a distal working end extending into the chamber in a lateral direction with respect to a longitudinal axis of the endoscopic instrument.

14. The method of claim 13, wherein the step of inserting the endoscopic instrument comprises inserting the endoscopic instrument into a colon to remove a polyp, and the polyp is severed and carried within the first channel outside the body lumen.

15. The method according to claim 13, wherein the chamber has a distal portion, a proximal portion and an intermediate portion between the distal and proximal portions, and the intermediate portion is expandable.

16. The method of claim 15, wherein the stiffening member is positionable proximal of the chamber.

17. The method of claim 15, wherein the step of expanding the chamber expands the chamber laterally to only one side of the longitudinal axis of the endoscopic instrument.

18. The method of claim 15, wherein the step of expanding the chamber expands the chamber laterally of the stiffening member.

19. The method according to claim 13, further comprising the step of illuminating at least one portion of the chamber or tissue provided at or protruding into the chamber to enable a visual inspection thereof.

* * * * *